US010251849B2

(12) United States Patent
Rawas-Qalaji et al.

(10) Patent No.: US 10,251,849 B2
(45) Date of Patent: Apr. 9, 2019

(54) SUBLINGUAL COMPOSITIONS INCLUDING EPINEPHRINE NANOPARTICLES

(71) Applicant: NOVA SOUTHEASTERN UNIVERSITY, Fort Lauderdale, FL (US)

(72) Inventors: Mutasem Rawas-Qalaji, Fort Lauderdale, FL (US); Ousama Rachid, Winnipeg (CA); Keith Simons, Winnipeg (CA); Estelle Simons, Winnipeg (CA)

(73) Assignee: Nova Southeastern University, Fort Lauderdale, FL (US)

( * ) Notice: Subject to any disclaimer, the term of this patent is extended or adjusted under 35 U.S.C. 154(b) by 0 days.

(21) Appl. No.: 15/262,961

(22) Filed: Sep. 12, 2016

(65) Prior Publication Data

US 2016/0374966 A1    Dec. 29, 2016

Related U.S. Application Data

(63) Continuation of application No. 14/408,038, filed as application No. PCT/US2013/045836 on Jun. 14, 2013, now abandoned.

(60) Provisional application No. 61/660,273, filed on Jun. 15, 2012.

(51) Int. Cl.
| A61K 31/137 | (2006.01) |
| A61K 9/00 | (2006.01) |
| A61K 9/20 | (2006.01) |
| A61K 9/14 | (2006.01) |

(52) U.S. Cl.
CPC ............ *A61K 31/137* (2013.01); *A61K 9/006* (2013.01); *A61K 9/0056* (2013.01); *A61K 9/14* (2013.01); *A61K 9/2013* (2013.01); *A61K 9/2054* (2013.01)

(58) Field of Classification Search
None
See application file for complete search history.

(56) References Cited

U.S. PATENT DOCUMENTS

| 5,143,731 A | 9/1992 | Viegas |
| 5,223,614 A | 6/1993 | Schromm et al. |
| 5,567,439 A | 10/1996 | Myers et al. |
| 5,587,172 A | 12/1996 | Cherukuri et al. |
| 5,622,716 A | 4/1997 | Barth |
| 5,622,717 A | 4/1997 | Fuisz |
| 5,654,003 A | 8/1997 | Fuisz et al. |
| 5,871,781 A | 2/1999 | Myers et al. |
| 6,024,981 A | 2/2000 | Khankari et al. |
| 6,221,392 B1 | 4/2001 | Khankari et al. |
| 6,264,981 B1 | 7/2001 | Zhang et al. |
| 6,309,663 B1 | 10/2001 | Patel et al. |
| 6,368,625 B1 | 4/2002 | Siebert et al. |
| 6,833,377 B2 | 12/2004 | Serdyuk |
| 9,877,921 B2 | 1/2018 | Rawas-Qalaji et al. |
| 2003/0021841 A1 | 1/2003 | Matharu et al. |
| 2003/0216413 A1 | 11/2003 | Root-Bernstein et al. |
| 2004/0076588 A1 | 4/2004 | Batycky et al. |
| 2004/0234611 A1 | 11/2004 | Ahlheim et al. |
| 2005/0130935 A1 | 6/2005 | Weidner |
| 2006/0093677 A1 | 5/2006 | Chickering et al. |
| 2007/0059361 A1* | 3/2007 | Rawas-Qalaji ...... A61K 9/0056 424/464 |
| 2007/0092553 A1 | 4/2007 | Tengler et al. |
| 2007/0154549 A1 | 7/2007 | Morton et al. |
| 2007/0202163 A1 | 8/2007 | Rawas-Qalaji et al. |
| 2007/0293580 A1 | 12/2007 | Hill |
| 2008/0032934 A1 | 2/2008 | Ellis-Behnke et al. |
| 2008/0069779 A1 | 3/2008 | Tamarkin et al. |
| 2009/0263476 A1* | 10/2009 | Jobdevairakkam .... A61K 9/006 424/452 |
| 2010/0035800 A1 | 2/2010 | Desai et al. |
| 2011/0182805 A1 | 7/2011 | DeSimone et al. |
| 2011/0223203 A1* | 9/2011 | Berkland ............. A61K 9/0075 424/400 |

(Continued)

FOREIGN PATENT DOCUMENTS

| CN | 101669917 | 3/2010 |
| CN | 101669917 A | 3/2010 |

(Continued)

OTHER PUBLICATIONS

Abdelbary et al., "Determination of the in Vitro Disintegration Profile of Rapidly Disintegrating Tablets and Correlation with Oral Disintegration," Int. J. Pharm., 292:29-41(2005).
"Adrenaline into Melanin," Br. Med J., 2:486 (1971).
Allen, "Rapid-Dissolve Technology: An Interview with Lloyd V. Allen, Jr. PhD, RPh," Int. J. Pharm. Compound., 7:449-450 (2003).
Aly et al., "Superdisintegants for Solid Dispersion to Produce Rapidly Disintegrating Tenoxicam Tablets via Camphor Sublimation," Pharm. Tech., 7:68-78 (2005).

(Continued)

*Primary Examiner* — Robert A Wax
*Assistant Examiner* — Danah Al-Awadi
(74) *Attorney, Agent, or Firm* — Fleit Gibbons Gutman Bongini & Bianco PC; Paul D. Bianco; Katharine Davis Wong

(57) ABSTRACT

The invention provides compositions including epinephrine nanoparticles and methods for therapeutic use of the compositions for the treatment of conditions responsive to epinephrine such as a cardiac event or an allergic reaction, particularly anaphylaxis. The epinephrine nanoparticles can be incorporated into orally-disintegrating and fast-disintegrating tablet pharmaceutical formulations and can significantly increase the sublingual bioavailability of epinephrine, and thereby reduce the epinephrine dose required. Additionally, the invention provides methods for fabrication of stabilized epinephrine nanoparticles for use in the described compositions.

17 Claims, 8 Drawing Sheets

(56) References Cited

U.S. PATENT DOCUMENTS

| | | |
|---|---|---|
| 2011/0250278 A1 | 10/2011 | Yuan |
| 2012/0322884 A1* | 12/2012 | Rawas-Qalaji ........ A61K 9/006 514/653 |
| 2014/0242177 A1 | 8/2014 | Rawas-Qalaji et al. |
| 2015/0164827 A1 | 6/2015 | Rawas-Qalaji et al. |
| 2016/0045457 A1 | 2/2016 | Rawas-Qalaji |
| 2016/0374966 A1 | 12/2016 | Rawas-Qalaji et al. |
| 2017/0000735 A1 | 1/2017 | Rawas-Qalaji et al. |
| 2017/0020827 A1 | 1/2017 | Rawas-Qalaji |
| 2017/0071881 A1 | 3/2017 | Rawas-Qalaji et al. |

FOREIGN PATENT DOCUMENTS

| | | |
|---|---|---|
| EP | 0159237 | 10/1985 |
| EP | 0159237 A1 | 10/1985 |
| EP | 2753321 A1 | 7/2014 |
| WO | 1994/09762 | 11/1993 |
| WO | WO 1994/009762 A1 | 5/1994 |
| WO | 2005/63203 | 12/2004 |
| WO | 2007/028247 | 3/2007 |
| WO | 2008-095284 | 8/2008 |
| WO | 2011/109340 | 9/2011 |
| WO | 2013-059629 | 4/2013 |
| WO | 2013/059629 | 4/2013 |
| WO | 2013059629 | 4/2013 |
| WO | 2014/007972 | 1/2014 |
| WO | 2014/153559 | 9/2014 |
| WO | WO 2014/153559 A1 | 9/2014 |

OTHER PUBLICATIONS

Aurora et al., "Oral Disintegrating Dosage Forms: An Overview," Drug Deliv. Technol., 5:50-54 (2005).
Bi et al., "Evaluation of Rapidly Disintegrating Tablets Prepared by a Direct Compression Method," Drug Dev. Ind. Pharm., 25:571-581 (1999).
Bi et al., "Preparation and Evaluation of a Compressed Tablet Rapid Disintegration in the Oral Cavity," Chem. Pharm. Bull., 44:2121-2127 (1996).
Birudaraj et al., "Buccal Permeation of Bispirone: Mechanistic Studies on Transport Pathways," J. Pharm. Sci., 94:70-78 (2004).
Chang et al., "Fast Dissolving Tablets," Pharm. Tech., 24:52-58 (2000).
Connors et al. In Chemical Stability of Pharmaceuticals: A Handbook for Pharmacists, Wiley-Interscience Publication: New York (1986).
Cunningham et al., "Comparative Pharmacokinetics of Oral Versus Sublingual Clonidine," J. Clin. Anesth., 6:430-433 (1994).
De Vries et al., "Developments in Buccal Drug Delivery," Crit. Rev. Ther. Drug Carr. Syst., 8:271-303 (1991).
Dobetti, "Fast-Melting Tablets: Developments and Technologies," PharmTech. Eur., 12:32-42 (2000).
Dor et al., "In Vitro Determination of Disintegration Time of Quick-Dissolve Tablets Using a New Method," Pharm. Dev. Technol., 5:575-577 (2000).
El-Arini et al., "Evaluation of Disintegration Testing of Different Fast Dissolving Tablets Using the Texture Analyser," Pharm. Dev. Technol., 7:361-371 (2002).
Fell et al., "Determination of Tablet Strength by the Diametral Compression Test," J. Pharm. Sci., 59:688-691 (1970).
Ganhao et al., "Evaluation of a Single Plasma Catecholamino Extraction Procedure Prior to High-Performance Liquid Chromatography and Electrochemical Detection," J. Chromatogr., 564:55-66 (1991).
Gu et al., "Is Epinephrine Administration by Sublingual Tablet Feasible for the First-Aid Treatment of Anaphylaxis? A Proof of Concept Study," Biopharm. Drug Dispos., 23:213-216 (2002).
Gu et al., "Epinephrine Absorption After Different Routes of Administration in an Animal Model," Biopharm. Drug Dispos., 20:401-405 (1999).
Hamilton et al., "Advanced Orally Disintegrating Tablets Bring Significant Benefits to Patients and Product Life Cycles," Drug Deliv. Technol., 5:34-37 (2005).
Hedenus et al., "Characterization of Instantaneous Water Absorption Properties of Pharmaceutical Excipients," Int. J. Pharm., 141:141-149 (2000).
Hjemdahl, "Catecholamine Measurements in Plasma by High-Performance Liquid Chromatography With Electrochemical Detection," Methods Enzymol., 142:521-534 (1987).
Hjemdahl, "Inter-Laboratory Comparison of Plasma Catecholamine Determinations Using Several Different Assays," Acta Physiol. Scand. Suppl., 527:43-54 (1984).
"Human Physiology: From Cells to Systems," Sherwood ed.; Brooks/Cole/Thomson Learning: Belmont, CA, 2004; Chapter 16, pp. 591-645.
Ishikawa et al., "Pharmacokinetics of Acetaminophen From Rapidly Disintegrating Compressed Tablet Prepared Using Microcrystalline Cellulose (PH-M-06) and Spherical Sugar Granules," Chem. Pharm. Bull., 49:230-232 (2001).
Ishikawa et al., "Preparation of Rapidly Disintegrating Tablet Using New Types of Microcrystalline Cellulose (PH-M Series) and Low Substituted-Hydroxypropylcellulose or Spherical Sugar Granule by Direct Compression Method," Chem. Pharm. Bull., 49:134-139 (2001).
Kroboth et al., "Triazopam Pharmalinetics After Intravenous, Oral, and Sublingual Administration," J. Clin. Psychopharmacol., 15:259-262 (1995).
Lieberman et al., "Joint Task Force on Practice Parameters," J. Allergy Clin. Immunol., 115:S483-S523 (2005).
Lieberman et al., "Use of Epinephrine in the Treatment of Anaphylaxis," Curr. Opin. Allergy Clin. Immunol., 3:313-318 (2003).
Mitra et al., "Peptides and Proteins—Buccal Absorption," Encyclopedia of Pharm. Tech., pp. 2081-2095 (2002).
Motwani and Lipworth, "Clinical Pharmacokinetics of Drugs Administered Buccaly and Sublingually," Clin. Pharmacokinet., 21:83-94 (1991).
Parakh et al., "A Review of Mouth Dissolving Tablet Technologies," Pharm. Tech 27:92-100 (2003).
Physical Tests: Dissolution (711); 22/17 ed., Rockville, MD: United States Pharmaceutical Convention Inc., 2007.
Price et al., "Single-Dose Pharmacokinetics of Sublingual Versus Oral Administration of Micronized 17β-Estradiol," Obstet. Gynecol., 89:340-345 (1997).
Rachid et al., "An Electronic Tongue: Evaluation of the Masking Efficacy of Sweetening and/or Flavoring Agents on the Bitter Taste of Epinephrine," AAPS PharmSciTech, 11:550-557 (2010).
Rachid et al., "Dissolution Testing of Sublingual Tablets: a Novel in Vitro Method," AAPS PharmSciTech, 12:544-552 (2011).
Rawas-Qalaji et al., "Fast-Disintegrating Sublingual Epinephrine Tablets: Effect of Drug and Tablet Dimensions on Tablet Characteristics," AAPS 7(52): Abstract W5220 (2005).
Rawas-Qalaji et al., "Sublingual Epinephrine Tablets Versus Intramuscular Injection of Epinephrine: Dose Equivalence for Potential Treatment of Anaphylaxis," J. Allergy Clin. Immunol., 117:398-403 (2006).
Rawas-Qalaji et al., "Fast-Disintegrating Sublingual Epinephrine Tablets: Effect of Epinephrine Load on Tablet Characteristics," AAPS PharmSciTech, 7:E1-E7 (2006).
Rawas-Qalaji et al., "Fast-Disintegrating Sublingual Epinephrine Tablets: Long Term Stability Study," AAPS 7(52) Abstract W5219 (2005).
Rawas-Qalaji et al., "Formulation of Fast-Disintegrating Sublingual Epinephrine Tablets for the First-Aid Treatment of Anaphylaxis Away from Health Care Facilities," AAPS 6(4) Abstract W4178(2004).
Rawas-Qalaji et al., "Evaluation of the Effect of Changing Tablet Dimensions on the Characteristics of Fast-Disintegrating Sublingual Epinephrine Tablets for the First-Aid Treatment of Anaphylaxis Away from Health Care Facilities," AAPS 6(4) Abstract W4179(2004).
Rawas-Qalaji et al., "Epinephrine for the Treatment of Anaphylaxis: Do All 40 mg Sublingual Epinephrine Tablet Formulations with Similar in Vitro Characteristics Have the Same Bioavailability?" Biopharm. Drug Dispos., 27:427-435 (2006).

(56) References Cited

OTHER PUBLICATIONS

Rawas-Qalaji et al., "Development of Epinephrine Nanoparticles Using Chitosan for the Treatment of Anaphylaxis," Poster Presentation at the 2011 AAPS Annual Meeting and Exposition, Oct. 23-27, 2011, Washington DC, Poster No. W4174.
Sastry et al., "Drug Delivery to the Oral Cavity: Molecule to Market," Chapter 13, pp. 311-316 (2005), Taylor & Francis, CRC Press.
Sastry et al., "Recent Technological Advances in Oral Drug Delivery—A Review," Pharm. Sci. Technol. Today, 3:138-145 (2000).
Saxena, "Sublingual Versus Vaginal Route of Misoprostol for Cervical Ripening Prior to Surgical Termination of First Trimester Abortions," Eur. J. Odst. Gynecol. Reprod. Biol., 125:19-113, (2006).
Scavone et al., "The Pharmacokinetics and Pharmacodynamics of Sublingual and Oral Alprazolam in the Post-Prandial State," Eur. J. Clin. Pharmacol., 42:439-443 (1992).
Schiermeier et al., "Fast Disposable Ibuprophen Tablets," Eur. J. Pharm. Sci., 15:295-305 (2002).
Sharma et al., "Manufacturing Technology Choices for Mouth Dissolving Tablets," Pharm. Tech. North America, 10-15 (2003).
Simons, "First-Aid Treatment of Anaphylaxis to Food: Focus on Epinephrine," J. Allergy Clin. Immunol., 113:837-844 (2004).
Simons et al., "Sublingual Epinephrine Administration in Humans: A Preliminary Study," J. Allergy Clin. Immunol., 113:S260 (2004).
Simons, "EpiPen Jr Versus EpiPen in Young Children Weighing 15 to 30 kg at Risk for Anaphylaxis," J. Allergy Clin. Immunol., 109:171-175 (2002).
Simons, "Outdated EpiPen and EpiPen Jr Autoinjection: Past Their Prime?" J. Allergy Clin. Immunol., 105:1025-1030 (2000).
Simons, "Anaphylaxis: Recent Advances in Assessment and Treatment," J. Allergy Clin. Immunol., 124(4):625-636 (2009).
Simons, "Anaphylaxis," J. Allergy Clin. Immunol., 125:S161-S181 (2010).
Simons, et al., "Epinephrine and Its Use in Anaphylaxis", Curr. Opin. Clin. Immunol., 10:354-361 (2010).
Spenard et al., "Placebo-Controlled Comparative Study of the Anxiolytic Activity and of the Pharmacokinetics of Oral and Sublingual Lorazepam in Generalized Anxiety," Biopharm. Drug Dispos., 9:457-464 (1988).
Sugimoto et al., "The Preparation of Rapidly Disintegrating Tablets in the Mouth," Pharm. Dev. Technol., 6:487-493 (2001).
Verm et al., "Current Status of Drug Delivery Technologies and Future Directions," Pharm. Technol., 25:1-4 (2001).
Watenabe et al., "New Compressed Tablet Rapidly Disintegating in Saliva in the Mouth Using Crystalline Cellulose and a Disintegrant," Biol. Pharm. Bull., 18:1308-1310 (1995).
International Search Report and Written Opinion dated Aug. 20, 2014 for PCT/US14/31579.
European Search Report for EP12842206 dated Mar. 31, 2015, 7 pages (national stage of PCT/US2012/61074 published as WO2013/59629).
Ting Qiao et al, Conjugation of catecholamines on magnetic nanoparticles coated with sulfonated chitosan, Colloids and Surfaces A: Physicochem, Eng. Aspects 380 (2011) 169-174.
Simons, Is epinephrine administration by sublingual table feasible for the first-aid treatment of anaphylaxes?, Biopharm Drup Dispos, Jul. 23, 2002, (5): 213-6, abstract.
International Preliminary Report on Patentability and Written Opinion for PCT/US13/45836 filed Jun. 14, 2013.
PubcheM: title: chemical and physical properties of epinephrine (only pertinent pp. 1 and 8), downloaded on Jun. 6, 2016, from http://dav.uspto.gove/webappapplicationViewer.html?casenumber_14778887#).
Spyros Papiris, et al, Clinical Review: Severe Asthma, Critical Care. vol. 6(1), p. 30-44, published online Nov. 22, 2001.
International Search Report dated Dec. 22, 2006, Written Opinion dated Dec. 22, 2006 and International Prelim Report on Patentability dated Dec. 10, 2007, for PCT/CA06/001472.
International Search Report dated Apr. 29, 2008, Written Opinion dated Apr. 29, 2008 and International Prelim Report on Patentability dated Apr. 11, 2009, for PCT/CA08/00197.
Office action dated Mar. 16, 2009 for U.S. Appl. No. 11/672,503.
Written Opinion dated Jan. 11, 2013 and International Prelim Report on Patentability dated Apr. 22, 2014, for PCT/US2012/061074.
International Search Report dated Jan. 11, 2013 for PCT/US2012/061074.
International Prelim Report on Patentability dated Sep. 4, 2012 for PCT/US2011/26604.
Office action dated Mar. 13, 2009 for U.S. Appl. No. 11/530,360.
For U.S. Appl. No. 13/582,346 office actions dated Sep. 12, 2013; Feb. 7, 2014 response dated Dec. 12, 2013.
Office Action dated Nov. 17, 2015 for EP 14-768584 (national stage of PCT/US2014/31579).
Birudaraj et al., 2004, J Pharm Sci 94.
Ishikawa et al., 2001, Chem Pharm Bull 49: 230-23.
Price et al., 1997, Obstet Gynecol 89: 340-345.
Kroboth et al., 1995, J Clin Psychopharmacol 15: 259-262.
Cunningham et al., 1994, J Clin Anesth 6: 430-433.
Scavone et al., 1992, Eur J Clin Pharmacol 42: 439-443.
Spenard et al., 1988, Biopharm Drug Dispos 9: 457-464.
Mitra et al., 2002, Encyclopedia of Pharm. Tech., 2081-2095.
Joint Task Force on Practice Parameters, 2005, J Allergy Clin Immunol 115: S483-S523.
Lieberman, 2003, Curr Opin Allergy Clin Immunol 3: 313-318.
Simons, 2004, J Allergy Clin Immunol 113: 837-844, First-Aid Treatment of Anaphylaxis to Food, 8 pgs.
Simons, F.E.R. J Allergy Clin Immunol 124(4):625-636 2009, Anaphylaxis: Recent Advances in Assessment and Treatment, 12 pgs.
Simons, F.E.R. J Allergy Clin Immunol 125:S161-181 2010, Anaphylaxis, 21 pgs.
Simons, K.J. et al. Current Opinion in Clinical Immunology 10:354-361 2010, Epinephrine and Its use in Anaphylaxis, 8 pgs.
Connors et al., 1986, In Chemical Stability of Pharmaceuticals: A Handbook for Pharmacists, Wiley-Interscience Publication: New York.
Gu et al., 2002, Biopharm Drug Dispos 23: 213-216.
Simons et al., 2004, J Allergy Clin Immunol 113: 425-438, S260 Abstract.
Rawas-Qalaji et al. J Allergy Clin Immunol 117:398-403 2006.
Rawas-Qalaji et al. Biopharm Drug Disposition 27 (9):427-435 2006.
AAPS PharmSciTech 12:544-552,2011.
Rachid, O. et al. AAPS PharmSciTech 12(2):544-552 2011.
USP/NF. Physical Tests: Dissolution (711); 22/17 ed. Rockville, MD: United States Pharmaceutical Convention Inc; 2007.
Rachid, O. et al. AAPS PharmSciTech 11(2):550-557 2010.
Rawas-Qalaji, AAPS PharmSciTech. 2006;7(2): Article 41.
Motwani et al., 1991, Clin Pharmacokinet 21: 83-94.
Nritten Opinion dated Apr. 29, 2011 for PCT/US11/26604 filed Mar. 1, 2010.
International Search Report dated Apr. 29, 2011 for PCT/US11/26604 filed Mar. 1, 2010.
Written Opinion dated Jan. 11, 2013 for PCT/US12/061074 filed Oct. 19, 2012.
International Search Report dated Jan. 11, 2013 for PCT/US12/061074 filed Oct. 19, 2012.
Abdelbary, G. et al., "Determination of the in vitro disintegration profile of rapidly disintegrating tablets and correlation with oral disintegration," Int. J. Pharm. 292:29-41 (2005).
Allen, L., "Rapid-Dissolve Technology: An Interview with Lloyd V. Allen, Jr. PhD, RPh," Int. J. of Pharma. Compounding 7:449-450 (2003).
Aly, A. et al., "Superdisintegrantsfor Solid Dispersion to Produce Rapidly Disintegrating TenoxicamTablets via Camphor Sublimation," Pharma. Tech.7:68-78 (2005).
Aurora, J. and Pathak, V., "Oral Disintegrating Dosage Forms: An Overview," Drug Deliv. Technol. 5:50-54 (2005).
Bi, Y.X. et al., Evaluation of Rapidly Disintegrating Tablets Prepared by a Direct Compression Method, Drug Dev. Ind. Pharm. 25:571-581 (1999).

(56) References Cited

OTHER PUBLICATIONS

Bi, Y. et al., "Preparation and Evaluation of a Compressed Tablet Rapidly Disintegrating in the Oral Cavity," Chem. Pharm. Bull, 44:2121-2127 (1996).
Birudaraj, R. et al., "Buccal Permeation of Buspirone: Mechanistic Studies on Transport Pathways," J. Pharm. Sci. 94:70-75 (2004).
Chang, R. et al., "Fast-Dissolving Tablets," Pharm. Tech. 24:52-58 (2000).
Cunningham, F. et al., "Comparative Pharmacokinetics or Oral versus Sublingual Clonidine," J. Clin. Anesth. 6:430-433 (1994).
De Vries, M. et al., "Developments in Buccal Drug Delivery," Crit. Rev. Ther. Drug Carr. Syst. 8:271-303 (1991).
Dobetti, L., "Fast-Melting Tablets: Developments and Technologies," Pharmaceutical Technology Europe 12:32-42 (2000).
Dor, P. and Fix, J., "In Vitro Determination of DisintegrationTime of Quick-Dissolve Tablets Using a New Method," Pharm. Dev. Technol. 5:575-577 (2000).
El-Arini, S. and Clas, S., "Evaluation of Disintegration Testing of Different Fast Dissolving Tablets Using the Texture Analyzer," Pharm. Dev. Technol. 7:361-371 (2002).
Fell, J.T. and Newton, J.M., "Determination of Tablet Strength by the Diametral-Compression Test," J. Pharm. Sci. 59:688-691 (1970).
Ganhao, M. et al., "Evaluation of a simple plasma catecholamine extraction procedure prior to high-performance liquid chromatography and electrochemical detection," J. Chromatogr, 564:55-66 (1991).
Gu, X. et al., "Is Epinephrine Administration by Sublingual Tablet Feasible for the First-Aid Treatment of Anaphylaxis? A Proof-0f-Concept Study," Biopharm. Drug Dispos. 23:213-216 (2002).
Gu, X., et al., "Epinephrine Absorption after Different Routes of Administration in an Animal Model," Biopharm Drug Dispos. 20: 401-405 (1999).
Hamilton, E. et al., "Advanced Orally Disintegrating Tablets Bring Significant Benefits to Patients & Product Life Cycles," Drug Deliv. Technol. 5:34-37 (2005).
Hedenus, P. et al., "Characterisation of instantaneous water absorption properties of pharmaceutical excipients," Int. J. Pharm. 141:141-149 (2000).
Hjemdahl, P., "Catecholamine Measurements in Plasma by High-Performance Liquid Chromatography with Electrochemical Detection," Methods in Enzymol. 142:521-534 (1987).
Hjemdahl, P., "Inter-laboratory comparison of plasma catecholamine determinations using several different assays," Acta Physiol. Scand. Suppl. 527:43-54 (1984).
*Human Physiology: From Cells to Systems*, Sherwood L., (ed.) Brooks/Cole/Thomson Learning: Belmont, CA, 2004; Chapter 16, pp. 591-645.
Ishikawa, T. et al., "Pharmacokinetics of Acetominophen from Rapidly Disintegrating Compressed Tablet Prepared Using Microcrystalline Cellulose (PH-M-06) and Spherical Sugar Granules," Chem Pharm. Bull. 49:230-232 (2001).
Ishikawa, T. et nl., "Preparation of Rapidly Disintegrating Tablet Using New Types of Microcrystalline Cellulose (PH-M Series) and Low Substituted-Hydroxypropylcellulose of Spherical Sugar Granules by Direct Compression Mehod," Chem. Pharm. Bull. 49:134-139 (2001).
Kroboth, P. et al., "Triazopam Pharmacokinetics After Intravenous, Oral, and Sublingual Administration," J. Clin. Psychopharmacol. 15:259-262 (1995).
Lieberman, P. et al., "Joint Task Force on Practice Parameters," J. Allergy Clin. Immunol. 115:S483-S523 (2005).
Lieberman, P., "Use of epinephrine in the treatment of anaphylaxis," Curr. Opin. Allergy Clin. Immunol. 3:313-318 (2003).
Mitra, A. et al., "Peptides and Proteins—Buccal Absorption," Encyclopedia of Pharm. Tech., pp. 2081-2095 (2002).
Motwani, J. and Lipworth, B., "Clinical Pharmacokinetics of Drugs Administered Buccally and Sublingually," Clin. Pharmacokinet. 21:83-94 (1991).
Parakh, S.R. and Gothoskar, A.V., "A Review of Mouth Dissolving Tablet Technologies," Pharm. Tech. 27:92-100 (2003).

Price, T.M. et al., "Single-Dose Pharmacokinetics of Sublingual Versus Oral Administration of Micronized 17β-Estradiol," Obstet. Gynecol. 89:340-345 (1997).
Rawas-Qalaji, M. et al., "Fast-Disintegrating Sublingual Epinephrine Tablets: Effect of Drug and Tablet Dimensions on Tablet Characteristics," AAPS 7(52):Abstract W5220 (2005).
Rawas-Qalaji, M. et al., "Sublingual epinephrine tablets versus intramuscular injection of epinephrine: Dose equivalence for potential treatment of anaphylaxis," J. Allergy Clin. Immunol. 117(2):398-403 (Feb. 2006).
Rawas-Qalaji, M. et al., "Fast-Disintegrating Sublingual Epinephrine Tablets: Effect of Epinhephrine Load on Tablet Characteristics," AAPS PharmSciTech 7(2) Article 41: E1-E7 (2006).
Rawas-Qalaji, M. et al., "Fast-Disintegrating Sublingual Epinephrine Tablets: Long Term Stability Study," AAPS 7(52) Abstract W5219 (2005).
Rawas-Qalaji, M. et al., "Formulation of Fast-Disintegrating Sublingual Epinephrine Tablets for the First-Aid Treatment of Anaphylaxis Away From Health Care Facilities," AAPS 6(4) Abstract W4178 (2004).
Rawas-Qalaji, M. et al., "Evaluation of the Effect of Changing Tablet Dimensions on the Characteristics of Fast-disintegrating Sublingual Epinephrine Tablets for the First-Aid Treatment of Anaphylaxis Away From Health Care Facilites," AAPS 6(4) Abstract 4179 (2004).
Rawas-Qalaji, M. et al., "Epinephrine for the Treatment of Anaphylaxis: Do All 40mg Sublingual Epinephrine Tablet Formulations with Similar in Vitro Characteristics Have the Same Bioavailability?" Biopharm. Drug Dispos. 27:427-435 (2006).
Sastry, S. et al., *Drug Del. to the Oral Cavity: Molecule to Market*, Chapter 13, pp. 311-316 (2005), eds. Taylor & Francis, CRC Press.
Sastry, S. et al., "Recent technological advances in oral drug delivery—a review," Pharm Sci. Technol. Today 3:138-145 (2000).
Scavone, J.M. et al., "The pharmacokinetics and pharmacodynamics of sublingual and oral alprazolam in the post-prandial state," Eur. J. Clin. Pharmacol. 42:439-443 (1992).
Schiermeier, S. and Schmidt, P., "Fast disporsable ibuprofen tablets," Eur. J. Pharm. Sci. 15:295-305 (2002).
Sharma, N. et al., "Manufacturing Technology Choices for Mouth Dissolving Tablets," Pharma. Tech. North America 10-15 (2003).
Simons, F. Estelle, "First-aid treatment of anaphylaxis to food: Focus on epinephrine," J. Allergy Clin. Immunol. 113:837-844 (2004).
Simons, K.J., et al., "Sublingual epinephrine administration in humans: A preliminary study," J. Allergy Clin. Immunol. 113 (Suppl. 1):S260 (2004).
Simons, F. Estelle, "EpiPen Jr versus EpiPen in young children weighing 15 to 30 kg at risk for anaphylaxis," J. Allergy Clin. Immunol. 109(1):171-175 (2002).
Simons, F. Estelle et al., "Outdated EpiPen and EpiPen Jr. autoinjectors: Past their Prime?" J. Allergy Clin. Immunol. 105:1025-1030 (2000).
Spenard, J. et al., "Placebo-Controlled Comparative Study of the Anxiolytic Activity and of the Pharmacokinetics of Oral and Sublingual Lorazepam in Generalized Anxiety," Biopharm. Drug Dispos. 9:457-464 (1988).
Sugimoto, M. et al., "The Preparation of Rapidly Disintegrating Tablets in the Mouth," Pharm. Dev. Technol. 6:487-493 (2001).
Verma, R. and Garg, S., "Current Status of Drug Delivery Technologies and Future Directions," Pharma. Technol. On-Line 25:1-4 (2001).
Watenabe, Y. et al., "New Compressed Tablet Rapidly Disintegrating in Saliva in the Mouth Using Crystalline Cellulose and a Disintegrant," Biol. Pharm. Bull. 18:1308-1310 (1995).
International Search Report dated Jan. 16, 2014 for PCT/US2013/045836.
Written opinion dated Jan. 16, 2014 for PCT/US2013/045836.
Rawan-Qalaji et all, Development of Epinephrine Nanoparticles Using Chitosan for the Treatment of Anaphylaxis, Poster presentation at the 2011 AAPS Annual Meeting and Exposition, Oct. 23-27, 2011, Washington DC, Poster No. W4174.
Adrenaline into Melanin, Br Med J, May 29, 2971, 2(5760): 486.

(56) References Cited

OTHER PUBLICATIONS

Sigma-Aldrich, Material Safety Data Sheet, Version 3.2, printed May 1, 2012.
Saxena, Sublingual versus vaginal route of misoprostol for cervical ripening prior to surgical termination of first timrester abortions, Eur J Obstet Gynecol Reprod Biol Mar. 1, 2006, 125(1): 109-13, abstract.
International Search Report dated Aug. 20, 2014, Written Opinion dated Aug. 20, 2014 and International Preliminary Examination Report dated Sep. 22, 2015 for PCT/US14/31579.
International Preliminary Report and Written Opinion dated May 1, 2014 for PCT/US2013/045836.

\* cited by examiner

SUBLINGUAL COMPOSITIONS INCLUDING EPINEPHRINE NANOPARTICLES

CROSS REFERENCE TO RELATED APPLICATIONS

This application is a continuation of U.S. application Ser. No. 14/408,038, filed Dec. 15, 2014; which is a National Stage of International Application No. PCT/US2013/045836, filed Jun. 14, 2013; which claims the benefit of the priority of U.S. Provisional Application No. 61/660,273, filed Jun. 15, 2012.

The aforementioned applications are hereby incorporated by reference in their entireties. The information incorporated is as much a part of the instant application as filed as if the text was repeated in the application, and should be treated (the incorporated information) as part of the text of the application as filed.

FIELD OF THE INVENTION

The invention generally relates to compositions and methods for treatment of conditions responsive to epinephrine (also known as adrenaline), particularly to compositions and methods for emergency treatment of conditions responsive to epinephrine, and most particularly to compositions including epinephrine nanoparticles for sublingual administration in treatment of conditions responsive to epinephrine.

BACKGROUND

Tablets that disintegrate or dissolve rapidly in the patient's mouth without the use of water are convenient for the elderly, young children, patients with swallowing difficulties, and in situations where water is not available. For these specially designed formulations, the small volume of saliva that is available is sufficient to disintegrate or dissolve a tablet in the oral cavity. The drug released from these tablets can be absorbed partially or entirely into the systemic circulation from the buccal mucosa or sublingual cavity, or can be swallowed as a solution to be absorbed from the gastrointestinal tract.

The sublingual route usually produces a faster onset of action than traditional orally-administered tablets and the portion absorbed through the sublingual blood vessels bypasses the hepatic first pass metabolic processes (Birudaraj et al., 2004, *J Pharm Sci* 94; Motwani et al., 1991, *Clin Pharmacokinet* 21: 83-94; Ishikawa et al., 2001, *Chem Pharm Bull* 49: 230-232; Price et al., 1997, *Obstet Gynecol* 89: 340-345; Kroboth et al., 1995, *J Clin Psychopharmacol* 15: 259-262; Cunningham et al., 1994, *J Clin Anesth* 6: 430-433; Scavone et al., 1992, *Eur Clin Pharmacol* 42: 439-443; Spenard et al., 1988, *Biopharm Drug Dispos* 9: 457-464).

Likewise, due to high buccal and sublingual vascularity, buccally- or sublingually-delivered drugs can gain direct access to the systemic circulation and are not subject to first-pass hepatic metabolism. In addition, therapeutic agents administered via the buccal or sublingual route are not exposed to the acidic environment of the gastrointestinal tract (Mitra et al., 2002, *Encyclopedia of Pharm. Tech.*, 2081-2095). Further, the buccal and sublingual mucosas have low enzymatic activity relative to the nasal and rectal routes. Thus, the potential for drug inactivation due to biochemical degradation is less rapid and extensive than other administration routes (de Varies et al., 1991, *Crit. Rev. Ther. Drug Carr. Syst.* 8: 271-303).

The buccal and sublingual mucosas are also highly accessible, which allows for the use of tablets which are painless, easily administered, easily removed, and easily targeted. Because the oral cavity consists of a pair of buccal mucosa, tablets, such as fast disintegrating tablets, can be applied at various sites either on the same mucosa or, alternatively, on the left or right buccal mucosa (Mitra et al., 2002, Encyclopedia of Pharm. Tech., 2081-2095). In addition, the buccal and sublingual routes could be useful for drug administration to unconscious patients, patients undergoing an anaphylactic attack, or patients who sense the onset of an anaphylactic attack.

Anaphylaxis is a sudden, severe systemic allergic reaction, which can be fatal within minutes. Epinephrine (Epi) is the drug of choice for the treatment of anaphylaxis worldwide (Joint Task Force on Practice Parameters, 2005, *J Allergy Clin Immunol* 115: S483-S523; Lieberman, 2003, *Curr Opin Allergy Clin Immunol* 3: 313-318; Simons, 2004, *J Allergy Clin Immunol* 113: 837-844). It is available as an injectable dosage form in ampoules or in autoinjectors, however these are underused when anaphylaxis occurs (Simons, F. E. R. *J Allergy Clin Immunol* 124(4):625-636 2009; Simons, F. E. R. *J Allergy Clin Immunol* 125:S161-181 2010). The drawbacks of Epi auto-injectors include high cost, perceived large size and bulkiness, limitations on repeated dosing (if required), fear and anxiety associated with the use of needles (especially in children), and dosing errors caused by incorrect techniques of administration (Simons, K. J. et al. *Current Opinion in Clinical Immunology* 10:354-361 2010). Furthermore, in aqueous solutions, epinephrine is unstable in the presence of light, oxygen, heat, and neutral or alkaline pH values (Connors et al., 1986, in *Chemical Stability of Pharmaceuticals: A Handbook for Pharmacists*, Wiley-Interscience Publication: New York) and thus has limited shelf-life; approximately one year.

The sublingual route of administration is a promising alternative route for epinephrine administration. The formulation of sublingual tablets of epinephrine would enable the development of tablets with a range of epinephrine doses to match the population on an mg/kg basis. Sublingual tablets of epinephrine would be easy to carry and self-administer eliminating the fear and anxiety associated with needles used in autoinjectors for young children, as well as readily providing the capability of multiple doses. Feasibility studies in humans and animals have shown that epinephrine can be absorbed sublingually (Gu et al., 2002, *Biopharm Drug Dispos* 23: 213-216; Simons et al., 2004, *J Allergy Clin Immunol* 113: 425-438). The recommended dose of epinephrine for the treatment of anaphylaxis is about 0.01 mg/Kg: usually about 0.2 mL to about 0.5 mL of a 1:1000 dilution of epinephrine in a suitable carrier. Based on historical and anecdotal evidence, an approximately 0.3 mg dose of epinephrine, by subcutaneous (SC) or intramuscular (IM) injection into the deltoid muscle, has been agreed upon as the dose required for the emergency treatment of anaphylaxis. Recent studies have demonstrated that if the approximately 0.3 mg dose is administered IM into the laterus vascularis (thigh) muscle, Epi plasma concentrations are higher and occur more quickly than SC or IM administration into the deltoid muscle. (Joint Task Force on Practice Parameters, 2005, *J Allergy Clin Immunol* 115: S483-S523; Lieberman, 2003, *Curr Opin Allergy Immunol* 3: 313-318; Simons, 2004, *J Allergy Clin Immunol* 113: 837-844)).

As stated above, epinephrine (Epi) is typically administered either subcutaneously (SC) or intramuscularly (IM) by injection. Thus, Epi injections are the accepted first aid means of delivering Epi and are administered either manually or by automatic injectors. It is recommended that persons at risk of anaphylaxis, and persons responsible for children at risk for anaphylaxis, maintain one or more automatic Epi injectors in a convenient place at all times.

Given the difficulties associated with manual subcutaneous (SC) or intramuscular (IM) administration of Epi, such as patient apprehension related to injections or the burden of an at risk person having to always maintain an Epi injector close at hand, there exists a need in the art for more convenient dosage forms which can provide immediate administration of Epi, particularly to a person undergoing anaphylaxis wherein the need for injection or Epi injectors is obviated.

Recently, a novel fast-disintegrating tablet suitable for sublingual (SL) administration of Epi was developed. See related U.S. applications: U.S. Provisional Patent Application No. 60/715,180; U.S. Provisional Patent Application No. 60/759,039; U.S. Utility patent application Ser. No. 11/672,503; and U.S. Utility patent application Ser. No. 11/530,360. Sublingual administration of 40 mg epinephrine as the bitartrate salt using these novel tablets resulted in a rate and an extent of epinephrine absorption similar to that achieved following intramuscular injections of 0.3 mg epinephrine in the thigh. Sublingual doses ranging from 5 to 40 mg epinephrine as the bitartrate salt were studied to achieve equivalent plasma concentrations. In an animal model, it was determined that a 40 mg epinephrine dose administered sublingually as a bitartrate salt in tablet form resulted in plasma epinephrine concentrations similar to those achieved by 0.3 mg epinephrine intramuscular (IM) injection (Rawas-Qalaji et al. *J Allergy Clin Immunol* 117:398-403 2006).

Without being bound by theory, it is thought that fabrication of epinephrine into nanoparticles and incorporation of the nanoparticles into a tablet formulation with pharmaceutically-acceptable carriers, penetration enhancers, and mucoadhesives will significantly increase the absorption of SL-administered epinephrine and will result in the reduction of SL epinephrine dose required.

SUMMARY OF THE INVENTION

Epinephrine (Epi) is life-saving in the treatment of anaphylaxis. In community settings, a first-aid dose of epinephrine in an amount of 0.15 mg or 0.3 mg is injected into the mid-outer thigh by patients or caregivers using an auto-injector such as an EpiPen® (epinephrine auto-injector 0.3/0.15 mg, Dey Pharma, L.P. Nappa, Calif.). Epi auto-injectors are under-used because of needle phobia, bulky size, and high cost; additionally, there are only two fixed doses, shelf-life is only 12-18 months, and unintentional injection and injury sometimes occur.

The instant invention circumvents the aforementioned problems by providing a fast-disintegrating epinephrine tablet formulation for anaphylaxis treatment. Although this formulation was designed with regard to anaphylaxis, it is equally effective and contemplated for use in treatment of any condition responsive to epinephrine such as cardiac events, i.e. cardiac arrest, and breathing difficulties, i.e. asthma, bronchial asthma, bronchitis, emphysema, and respiratory infections.

In a validated rabbit model, this fast-disintegrating epinephrine tablet formulation resulted in plasma epinephrine concentrations similar to those achieved after a 0.3 mg epinephrine intra-muscular injection (Rawas-Qalaji et al. *J Allergy Clin Immunol* 117:398-403 2006). Furthermore, epinephrine was stable in these fast-disintegrating tablets for at least seven years.

In one aspect, the invention provides epinephrine nanoparticles. The epinephrine can be either an epinephrine base or an epinephrine bitartrate salt.

The invention also provides stabilized epinephrine nanoparticles.

In another aspect, the invention provides a composition including epinephrine nanoparticles capable of enhancing the sublingual bioavailability of epinephrine for the emergency treatment of anaphylaxis.

The invention additionally provides a method for fabrication of stabilized epinephrine nanoparticles and incorporation of the fabricated nanoparticles into orally-disintegrating and fast-disintegrating tablets. The fabrication method includes combining a pre-determined amount of epinephrine (epinephrine base or epinephrine bitartrate salt) and a solvent in a reaction chamber to form a mixture and exposing the mixture to at least one pass at a pre-determined pressure and a pre-determined temperature. The pre-determined pressure ranges from about 8,000 psi to 30,000 psi. The predetermined temperature ranges from 8.3 to 43.3° C. The solvent with which the epinephrine is combined can be water with or without sodium metabisulfite, isopropyl alcohol (ISP), methanol, acetonitrile, acetone, hexane, chloroform, dichloromethane (DCM), tetrahydrofuran (THF), ethyl acetate, phosphoric acid, and acetic acid.

As described herein, buccal or sublingual oral disintegrating tablets (ODTs) are distinguished from conventional sublingual tablets, lozenges, or buccal tablets by the ODTs' ability to fully dissolve or disintegrate in less than about one minute in the mouth.

The fabrication method for stabilized epinephrine nanoparticles can also include exposing the mixture of epinephrine and solvent to a second pass at a different pre-determined pressure and a different pre-determined temperature from that of the first pass.

Additionally, nanoparticles fabricated by the method can be lyophilized (freeze-dried).

In another aspect, the invention provides a pharmaceutical composition including epinephrine nanoparticles formulated for buccal or sublingual administration.

The invention also provides a pharmaceutical composition including epinephrine nanoparticles and a pharmaceutically-acceptable carrier for buccal or sublingual administration.

The phrase "pharmaceutically-acceptable carrier" refers to an inactive and non-toxic substance used in association with an active substance, i.e. epinephrine, especially for aiding in the application of the active substance. Non-limiting examples of pharmaceutically-acceptable carriers are diluents, binders, disintegrants, flavorings, fillers, and lubricants. Pharmaceutically-acceptable carriers can have more than one function, i.e. a filler can also be a disintegrant. Additionally, pharmaceutically-acceptable carriers may also be referred to as non-medicinal ingredients (NMIs).

The invention also provides a pharmaceutical composition, for buccal or sublingual administration, including epinephrine nanoparticles and at least one of a pharmaceutically-acceptable carrier, a penetration enhancer, and a mucoadhesive. The pharmaceutical composition can further include at least one of a taste enhancer and a sweetening agent and mouthfeel enhancer. A non-limiting example of a taste enhancer is citric acid. Citric acid masks the bitter taste of epinephrine. A non-limiting example of a sweetening agent and mouthfeel enhancer is mannitol. The pharmaceutical composition can further include at least one of a filler, a lubricant, and a disintegrant. Non-limiting examples include microcrystalline cellulose (filler), magnesium stearate (lubricant), and hydroxypropyl ethers of cellulose (disintegrant).

Additionally, the invention provides a pharmaceutical composition including epinephrine nanoparticles, in which the bitter taste of the epinephrine is masked by a taste enhancer. A non-limiting example of a taste enhancer is citric acid.

In another aspect, the invention provides a method for enhancing sublingual bioavailability of epinephrine in a subject in need thereof including steps for providing a composition including epinephrine nanoparticles and at least one pharmaceutically-acceptable carrier and administering the composition to the subject. The described fast-disintegrating epinephrine tablets enhance bioavailability of epinephrine by releasing epinephrine within sixty seconds of administration.

In another aspect, the invention provides a method for treating a condition responsive to epinephrine in a subject in need thereof including steps for providing a composition including epinephrine nanoparticles and at least one pharmaceutically-acceptable carrier and administering the composition to the subject. Conditions responsive to epinephrine react to administration of epinephrine. Non-limiting examples of conditions responsive to epinephrine include a cardiac event, i.e. cardiac arrest, or an allergic reaction, i.e. anaphylaxis, asthma, or bronchial asthma.

The phrase "effective amount" refers to the amount of a composition necessary to achieve the composition's intended function.

The phase "therapeutically-effective amount" refers to the amount of a composition required to achieve the desired function, i.e. treatment of the condition responsive to epinephrine.

In another aspect, the invention provides a method for treating a breathing difficulty in a subject in need thereof including steps for providing a composition including epinephrine nanoparticles and at least one pharmaceutically-acceptable carrier and administering the composition to the subject. Breathing difficulties responsive to epinephrine include, but are not limited to, breathing difficulties associated with anaphylaxis, asthma, bronchial asthma, bronchitis, emphysema, and respiratory infections.

The invention additionally provides a method for treatment of an allergic emergency in a subject diagnosed with or suspected of having an allergic emergency including steps for providing a composition including epinephrine nanoparticles and at least one pharmaceutically-acceptable carrier and administering the composition to the subject. Non-limiting examples of allergic emergencies are anaphylaxis, asthma, and bronchial asthma.

In an additional aspect, the invention provides a method for treatment of a cardiac event in a subject diagnosed with or suspected of having a cardiac event including steps for providing a composition including epinephrine nanoparticles and at least one pharmaceutically-acceptable carrier and administering the composition to the subject. A non-limiting example of a cardiac event is cardiac arrest.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

DETAILED DESCRIPTION OF THE INVENTION

Figure 1:
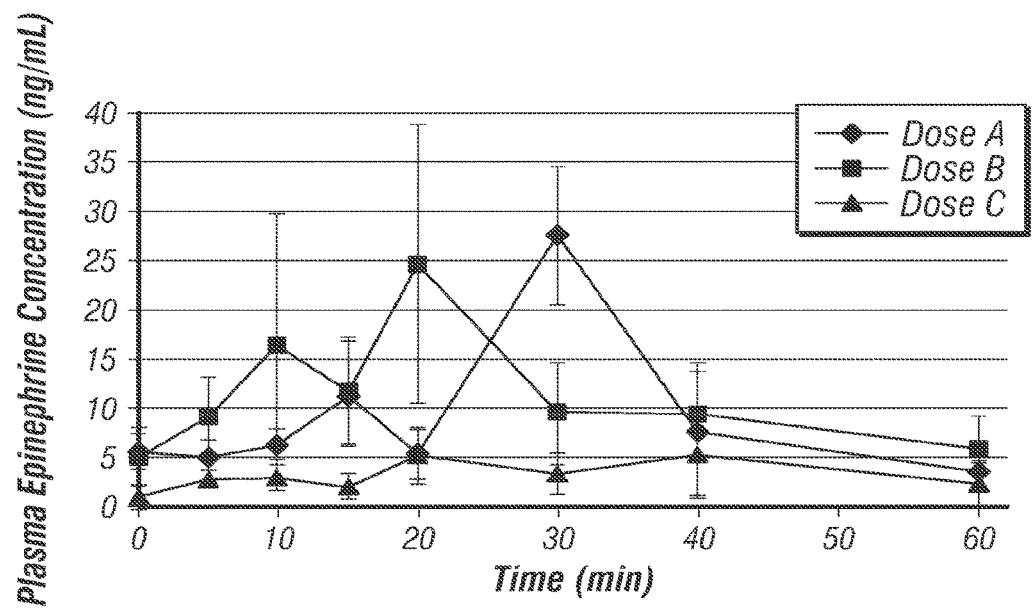
FIG. 1 is a graph showing mean±SD plasma epinephrine concentration versus time plots.

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions and methods and any further application of the principles of the invention as described herein, are contemplated as would normally occur to one skilled in the art to which the invention relates.

Example 1: Epinephrine Sublingual Tablets—In Vivo Studies

Epinephrine tablets were developed and evaluated as described in the related application; U.S. Patent Provisional Application No. 61/550,359, filed on Oct. 21, 2011. The tablet identified as "Formulation 7" was used for the in vivo studies described herein.

The rate and extent of epinephrine absorption from the sublingual tablets were studied in a validated rabbit model using a parallel-dose design. The administration of various epinephrine dosage forms, the protocol of the animal study, and the extraction analysis of epinephrine from collected blood samples were previously described. See Rawas-Qalaji et al. *J Allergy Clin Immunol* 117(2):398-403 2006. Results demonstrated that mean (±SD) area under the curve (AUC), maximum plasma concentration ($C_{max}$), and time at $C_{max}$ ($T_{max}$) after administration of 40 mg epinephrine sublingual tablets and epinephrine intramuscular injections were not significantly different (P>0.05). However, the sublingual tablet formulation resulted with a plasma epinephrine concentrations similar to those achieved using a 0.3 mg intramuscular epinephrine injection in an animal model. See Rawas-Qalaji et al. *J Allergy Clin Immunol* 117(2):398-403 2006. Further, the sublingual epinephrine tablets have a shelf-life of approximately seven years.

The sublingual epinephrine tablets (40 mg) were developed by substitution of non-medicinal ingredients (NMIs). By incorporation of mannitol, microcrystalline cellulose (Ceolus™, Asahi Kasei Company) and a disintegrant (Ludiflash®, BASF The Chemical Company) into the tablets, total epinephrine release within sixty seconds was achieved (assessed in vitro). (Rachid et al. *AAPS PharmSci Tech* 12(2): 544-552 2011). By addition of citric acid, the bitter taste of epinephrine was masked (assessed by electronic tongue). (Rachid et al. *AAPS PharmSci Tech* 11(2):550-557 2010).

The rate and extent of epinephrine absorption from the sublingual tablets was studied in a validated rabbit model using a parallel-dose design. The positive control was 0.3 mg intramuscular injection (of epinephrine) from a commercially-available EpiPen® (epinephrine auto-injector 0.3/0.15 mg, Dey Pharma, L.P. Nappa, Calif.). The negative control was a sublingual tablet containing only non-medicinal ingredients (NMIs) (contained no epinephrine).

Tablets were placed under the tongue for two minutes. Blood samples were collected at frequent intervals through an indwelling arterial catheter. Epinephrine concentrations were measured using high-performance liquid chromatography (HPLC) with electrochemical detection. Plasma concentration versus time data was analyzed using standard pharmacokinetic equations and WinNonlin® program (Pharsight Corporation).

The mean±SD maximum plasma concentration ($C_{max}$) of 31.7±10.1 ng/mL at a peak time ($T_{max}$) of twenty minutes and an area under the curve (AUC) of 678.0±149.0 ng/mL/min after administration of sublingual epinephrine (40 mg) did not differ significantly from the $C_{max}$ of 27.6±7.0 ng/mL at a $T_{max}$ of thirty minutes with an AUC of 592.0±122.3 ng/mL/min after an epinephrine (0.3 mg) intramuscular injection in the thigh (p≤0.05).

TABLE 1.1

Epinephrine Sublingual Tablets-Formulation 7

| Tablet Contents | Ingredients | Type | Weight (mg) | Percentage % |
|---|---|---|---|---|
| 1 | Active Ingredient | *epinephrine bitartrate | 72.77 | 36.39 |
| 2 | Filler | **Ceolus™, MCC (PH-M-06) | 11.17 | 5.59 |
| 3 | Filler | **Ceolus™, MCC (PH-301) | 66.80 | 33.40 |
| 4 | Filler | ***Ludiflash ® (88% mannitol) | 34.10 | 17.05 |
| 5 | Flavor | †Citric Acid | 2.50 | 1.25 |
| 6 | Disintegrant | ‡L-HPC (LH-11) | 8.66 | 4.33 |
| 7 | Lubricant | Mg Stearate | 4.0 | 2.00 |
| | Tablet Weight | | 200.00 | 100.00 |

*Each tablet contained 72.77 mg Epinephrine bitartrate which is equivalent to 40 mg Epinephrine base.
**Ratio of MCC (Ph-301) and MCC (PH-M-06) was kept at 6:1.
***Ludiflash ® consists of an average of 88% mannitol, Ludiflash ® at 17.05% will contain 15% mannitol.
†Ratio of Epinephrine bitartrate and citric acid was kept at 29:1.
‡Ratio of total MCC and L-HPC was kept at 9:1.
MCC (PH-M-06) particle size is 7 μm. MCC (PH-301) particle size is 50 μm.
Ludiflash ® particle size is 200 μm.

TABLES 1.2A-C

Epinephrine bioavailability after sublingual administration of different epinephrine doses and epinephrine intramuscular injection into the thigh.

| Rabbit Id | $AUC_{0-60\ min}$ (ng/mL/min) | $C_{baseline}$ (ng/mL) | $C_{max}$ (ng/mL) | $T_{max}$ |
|---|---|---|---|---|
| A) Dose A (EpiPen ® 0.3 mg I.M. Injection) | | | | |
| 2 | 574.6 | 5.6 | 29.7 | 30.0 |
| 9 | 823.6 | 4.2 | 37.3 | 30.0 |
| 10 | 473.7 | 3.7 | 21.6 | 30.0 |
| 4 | 590.5 | 5.3 | 33.4 | 30.0 |
| 11 | 579.4 | 6.0 | 24.1 | 30.0 |
| 12 | 510.1 | 9.0 | 19.4 | 30.0 |
| Mean | 592.0 | 5.6 | 27.6 | 30.0 |
| SD | 122.3 | 1.9 | 7.0 | 0.0 |
| B) Dose B (Epinephrine 40 mg Sublingual Tablet) | | | | |
| 3 | 811.3 | 2.0 | 37.9 | 20.0 |
| 6 | 863.7 | 3.9 | 39.5 | 10.0 |
| 8 | 541.9 | 3.9 | 18.3 | 30.0 |
| 11 | 561.4 | 5.5 | 23.4 | 20.0 |
| 12 | 611.7 | 9.9 | 39.1 | 20.0 |
| Mean | 678.0 | 5.0 | 31.7 | 20.0 |
| SD | 149.0 | 3.0 | 10.1 | 7.1 |

TABLES 1.2A-C-continued

Epinephrine bioavailability after sublingual administration of different epinephrine doses and epinephrine intramuscular injection into the thigh.

| Rabbit Id | $AUC_{0-60\ min}$ (ng/mL/min) | $C_{baseline}$ (ng/mL) | $C_{max}$ (ng/mL) | $T_{max}$ |
|---|---|---|---|---|
| C) Dose C (Placebo Sublingual Tablet) | | | | |
| 4 | 259.0 | 0.3 | 8.9 | 40.0 |
| 5 | 332.0 | 0.2 | 11.7 | 40.0 |
| 7 | 226.5 | 0.2 | 9.0 | 20.0 |
| 3 | 241.2 | 0.5 | 6.6 | 60.0 |
| 6 | 136.2 | 2.2 | 3.6 | 30.0 |
| 8 | 126.1 | 3.0 | 5.0 | 10.0 |
| Mean | 220.1 | 1.1 | 7.5 | 33.3 |
| SD | 78.0 | 1.2 | 3.0 | 17.5 |

TABLE 1.3

Plasma epinephrine concentration versus time plots after administration of epinephrine or placebo sublingually and after epinephrine intramuscular injection.
Mean (±SD) Epinephrine Plasma Concentration (ng/mL)

| Time (min) | Dose A | Dose B | Dose C |
|---|---|---|---|
| 0 | 5.6 ± 1.9 | 5.0 ± 3.0 | 1.1 ± 1.2 |
| 5 | 4.8 ± 1.9 | 9.1 ± 4.0 | 2.9 ± 1.0 |
| 10 | 6.4 ± 1.5 | 16.3 ± 13.5 | 3.0 ± 1.3 |
| 15 | 11.5 ± 5.8 | 11.8 ± 5.4 | 2.1 ± 1.4 |
| 20 | 5.3 ± 2.5 | 24.6 ± 14.1 | 5.2 ± 2.9 |
| 30 | 27.6 ± 7.0 | 9.5 ± 5.2 | 3.5 ± 2.1 |
| 40 | 7.5 ± 6.3 | 9.5 ± 5.1 | 5.3 ± 4.3 |
| 60 | 3.6 ± 0.8 | 5.8 ± 3.5 | 2.4 ± 2.2 |

The results are promising in that the epinephrine sublingual tablet formulation has similar absorption time ($T_{max}$) and plasma epinephrine concentration ($C_{max}$) to intramuscular injection. FIG. 1 shows a graph plotting plasma epinephrine concentration versus time after administration of epinephrine intramuscular injection (Dose A) and after administration of epinephrine (Dose B) or placebo (Dose C) sublingually. Mean (±SD) AUC, $C_{max}$, and $T_{max}$ after administration of 40 mg epinephrine sublingual tablets and epinephrine intramuscular injections were not significantly different (P>0.05).

Example 2: Long-Term Stability of Epinephrine Tablets

Need for Sublingual Epinephrine Tablets

For the emergency treatment of anaphylaxis, prompt intramuscular injection of epinephrine in thigh muscle is the drug of choice and it is the only available dosage form for the first-aid emergency treatment (Kemp et al. *Allergy* 63(8):1061-1070 2008; McLean-Tooke et al. *BMJ* 327 (7427):1332-1335 2003; Simons et al. *Curr Opin Allergy Clin Immunol* 10(4):354-361 2010; Soar et al. *Resuscitation* 77(2):157-169 2008). Epinephrine auto-injectors such as EpiPen®, EpiPen Jr® (Dey Pharma L.P. Nappa, Calif.), Twinject 0.3 mg®, and Twinject 0.15® (Shionogi Pharma, Inc. Atlanta, Ga.) are prescribed for the first-aid emergency treatment of anaphylaxis. However, self-injectable epinephrine is underutilized when anaphylaxis occurs due to several drawbacks (Simons, F E *Ann Allergy Asthma Immunol* 102(5):403-409 2009; Simons, F E R *Ann Allergy Asthma Immunol* 94(5):534-538 2005), including a short shelf-life of approximately a year.

Epinephrine is extensively metabolized after oral administration by the catechol-O-methyltransferase in the gastrointestinal tract and by monoamine oxidase in the gastrointestinal tract and in the liver (Hoffman et al. *Neurotransmission: The Automatic and Somatic Motor Nervous Systems* In: Hardman et al. editors Goodman & Gilman's *The Pharmacological Basis of Therapeutics* 9$^{th}$ edition New York: McGraw-Hill Companies Inc. pages 115-153 2001). Drugs that can be absorbed sublingually bypass potential metabolic conversion in the gastrointestinal tract and hepatic first-pass metabolism, and reach the systemic circulation in a pharmacologically active form (Bredenberg et al. *Eur J Pharm Sci* 20(3):327-334 2003; Glover et al. *Nicotine Tob Res* 4(4):441-450 2002; Guez, S *Chem Immunol Allergy* 82:62-76 2003; Rawas-Qalaji et al. *J Allergy Clin Immunol* 117(2):398-403 2006; Rawas-Qalaji et al. *Biopharm Drug Dispos* 27(9):427-435 2006; Saxena et al. *Eur J Obstet Gynecol Reprod Biol* 125(1):109-113 2006 (Epub 2005)).

Thus, the sublingual route is a promising alternative route for epinephrine administration. The high vascularity of the sublingual mucosa and the low molecular weight of epinephrine facilitate rapid absorption directly into the venous circulation through the sublingual and frenular veins.

Considering the above, epinephrine tablets, especially those with a shelf-life of more than a year, are pharmaceutically desirable.

This study was undertaken to evaluate the long term stability of epinephrine in the fast-disintegrating tablets described herein during manufacturing processes and after pre-determined periods of storage.

Summary of Methods and Results of Stability Studies

Epinephrine tablets, developed and evaluated as described in the related applications (U.S. Utility patent application Ser. No. 11/672,503, filed on Feb. 7, 2007 and U.S. Utility patent application Ser. No. 11/530,360, filed on Sep. 8, 2006) were tested and reported to be stable for at least twenty months. This same tablet formulation was analyzed after seven years of storage.

The analysis was performed using standard USP chromatography methods using high performance liquid chromatography with ultraviolet (UV) detector. Any potential oxidative products were extracted and analyzed using UV spectrophotometer. Results demonstrated that mean epinephrine dose in all the stored tablets did not differ significantly from controls and were within USP compedial limits for tablet content. Also, the absorptivity of oxidative products was below 0.1 for tablets stored at 25° C. and below 0.01 for all other tablets. Results show that epinephrine in these sublingual tablets remains stable for at least seven years.

Epinephrine tablets (10 mg, 20 mg, and 40 mg) were manufactured by direct compression and tested for quality control. Tablets were stored in opaque containers with desiccants at 25° C., 5° C., or 5° C. under nitrogen. Six or three tablets were randomly selected from each storage condition at six and twelve months for 10 mg and 20 mg tablets, twenty months for 40 mg tablets, and 7 years for 10 mg, 20 mg, and 40 mg tablets. Tablets were inspected visually for changes in color and analyzed by HPLC-UV and UV spectrophotometer for measurement of epinephrine content and absorbance of oxidative products of epinephrine after storage, respectively. Remaining epinephrine dose and the absorptivity of oxidative products were calculated and statistically analyzed versus controls (p<0.05).

Pale yellow discoloration was observed only in 40 mg epinephrine tablets stored for twenty months and seven years at 25° C. Mean epinephrine dose in all the stored tablets did not differ significantly from controls and were within USP compedial limits for tablet content. Absorptivity of oxidative products was below 0.1 for tablets stored at 25° C. and below 0.01 for all other tablets (0.2 is the USP limit for impurities).

Materials (−)-Epinephrine (+) bitartrate, (−)-3,4-dihydroxy-α-[(methylamino)methyl]benzyl alcohol (+)-tartrate (1:1) salt, was purchased from Sigma-Aldrich (St. Louis, Mo.). Ceolus® PH-301 (microcrystalline cellulose) with a mean particle size of 50 μm was supplied by Asahi Kasei Chemicals Corp (Tokyo, Japan) and low-substituted hydroxypropyl cellulose (LH11) with a mean particle size of 50 μm was supplied by Shin-Etsu Chemical Co (Tokyo, Japan). Magnesium stearate was purchased from Mallinckrodt Baker (Phillipsburg, N.J.).

In aqueous solutions, epinephrine is unstable in the presence of oxygen, light, heat, and neutral or alkaline pH values. Epinephrine decomposes into the pharmacologically toxic colored molecules, adrenochrome and adrenolutin, which can be eventually oxidized to melanin (*Br Med J* 5760(2):486 1971; Connors et al. *Chemical Stability of Pharmaceuticals: A Handbook for Pharmacists* 2nd edition New York: Wiley-Interscience Publication 1986). As a powder, epinephrine base and epinephrine salt should be stored in cool, dry, and light-resistant containers according to USP (USP/NF. Official Monograph: Epinephrine. 31/26 ed. Rockville, Md.: United States Pharmacopeial Convention, Inc. 2008) and Material Safety Data Sheet (MSDS) (Material Safety Data Sheet: (−)-Epinephrine (+)-bitartrate salt. Saint Louis, Mo.: Sigma-Aldrich; [Jun. 19, 2009]; available from the Sigma-Aldrich catalog).

Manufacturing and Quality Control of Tablets

Three fast-disintegrating tablet formulations containing epinephrine bitartrate equivalents to 10 mg, 20 mg, and 40 mg epinephrine were manufactured by direct compression. These tablets were formulated using microcrystalline cellulose, low-substituted hydroxylpropyl cellulose, and magnesium stearate as described (Rawas-Qalaji et al. *Drug Dev Ind Pharm* 33(5):523-530 2007; Rawas-Qalaji et al. *AAPS PharamSci Tech* 7(2): Article 41 2006). The tablet weight was 150 mg. All excipients were used as supplied and kept under low humidity condition before mixing. The mixing process was performed in a nitrogen-preflushed opaque glass container using three-dimensional manual mixer (Inversina, Bioengineering AG, Wald, Switzerland). The nitrogen gas was obtained from a local supplier and was used as supplied. The powder mixture of the three tablet formulations was compressed right after mixing at a pre-selected compression force for each tablet formulation based on our previous results (Rawas-Qalaji et al. *AAPS PharamSci Tech* 7(2): Article 41 2006) that ensures rapid tablet disintegration and wetting while retaining sufficient hardness to withstand shipping and handling.

All tablet formulations were tested for tablet weight variation, drug content uniformity, and friability using the harmonized USP methods and criteria (USP/NF. Physical Tests: Tablet Friability (1216). 26/21 ed. Rockville, Md.: United States Pharmacopeial Convention, Inc.; 2003; USP/NF. Physical Tests: Uniformity of Dosage Units (905). 31/26 ed. Rockville, Md.: United States Pharmacopeial Convention, Inc.; 2008). Drug content was analyzed using a high performance liquid chromatography (HPLC) system with ultra violet (UV) detection (Waters Corp., Milford, Mass.) as described below and tablet friability was measured using USP Friability instrument (Pharma Test Apparatebau GmbH, Hainburg, Germany). Tablet hardness, disintegration time, and wetting time were tested as described below by randomly selecting six tablets from each formulation. The mean±standard deviation (SD) and percentage of coefficient of variation (RSD %) were calculated.

Hardness (H):

The H or the crushing tolerance of tablets was measured using an Erweka® hardness tester (Heusenstamm, Germany).

Disintegration Time (DT):

A relatively simple method with rigorous conditions was developed to evaluate the DT of rapidly disintegrating tablets. Each individual tablet was dropped into 10 ml glass test tube (1.5 cm diameter) containing 2 ml distilled water, and the time required for complete tablet disintegration was observed visually and recorded using a stopwatch. The visual inspection was enhanced by gently rotating the test tube at a 45° angle, without agitation, to distribute any tablet particles that might mask any remaining undisintegrated portion of the tablets (Rawas-Qalaji et al. *Drug Dev Ind Pharm* 33(5):523-530 2007; Rawas-Qalaji et al. *AAPS PharamSci Tech* 7(2): Article 41 2006).

Wetting Time (WT):

Tablet WT was measured by a procedure modified from that reported by Bi et al. (*Chem Pharm Bull.* 44(11):2121-2127 1996). The tablet was placed at the center of 2 layers of absorbent paper fitted into a rectangular plastic dish (11 cm×7.5 cm). After the paper was thoroughly wetted with distilled water, excess water was completely drained out of the dish. The time required for the water to diffuse from the wetted absorbent paper throughout the entire tablet was then recorded by using a stopwatch (Rawas-Qalaji et al. *Drug Dev Ind Pharm* 33(5):523-530 2007; Rawas-Qalaji et al. *AAPS PharamSci Tech* 7(2): Article 41 2006).

Analysis of Tablets for Epinephrine Content Uniformity:

Ten tablets out of 30 tablets were randomly selected from each formulation. Each tablet was allowed to disintegrate in 2.0 mL solvent containing 0.1 M perchloric acid and 0.1 mM sodium metabisulfite to maintain the stability of epinephrine, vortexed to dissolve all the epinephrine in the tablet, and then centrifuged. Aliquots of 50 μL were withdrawn and diluted to 2.0 mL by the solvent. Drug content was analyzed using 2690 Alliance-Waters™ HPLC system with UV detection (Waters Corp., Milford, Mass.) according to USP method for epinephrine injection analysis (USP/NF. Official Monograph: Epinephrine Injection. 31/26 ed. Rockville, Md.: United States Pharmacopeial Convention, Inc.; 2008). Calibration curve was linear over the range of 6.125 to 600.0 μg/mL with correlation of coefficients ($R^2$) of >0.99. The coefficient of variation (RSD %) of the system reproducibility at concentrations of 6.125 and 600 μg/mL (n=5 each) were 1.07% and 0.40%, respectively. The intra- and interassay CV % were 0.40 and 0.70% (n=2) and 6.9 and 3.5% (n=6), respectively.

Storage and Sampling of Tablets for Stability Testing

Each of the three tablet formulations, 10 mg, 20 mg, and 40 mg, was divided into three equal portions and immediately stored in tightly closed, opaque, 1 oz capacity, polytetrafluoroethylene (PTFE) containers (Berry Plastics Corporation, Evansville, Ind.) with desiccants. The tablets were subjected to a series of conditions at which tablets are commonly stored. Container 1 was stored at 25° C. (room temperature), container 2 was stored at 5° C. (refrigerator temperature), and container 3 was flushed with nitrogen before being tightly closed and stored at 5° C. For the analysis of epinephrine content, six tablets were randomly sampled from the three containers after 6 and 12 months of storage for 10 and 20 mg tablets and after 20 months of storage for 40 mg tablets. After 7 years of storage, 3 tablets were sampled from the three containers of all tablets for the analysis of both epinephrine content and oxidative products. For the tablets stored under nitrogen at 5° C. (container 3), the containers were re-flushed with nitrogen after sampling, before being sealed and stored for the next sampling time.

Evaluation of Tablet Stability after Storage

The sampled tablets were visually examined for any color changes after storage and analyzed for epinephrine content by HPLC, and the UV absorbance of oxidative products were measured by spectrophotometer.

HPLC Analysis of Epinephrine Content:

The sampled tablets from each formulation and storage condition were analyzed individually. Epinephrine and any oxidative products were extracted, diluted and analyzed by HPLC-UV using the same procedure under "Analysis of Tablet for Epinephrine Content Uniformity" in a previous section.

UV Absorbance of Oxidative Products:

Three tablets were allowed to disintegrate and were vortexed to dissolve all the epinephrine bitartrate and any oxidative products in diluted hydrochloric acid (1 in 200) and then centrifuged. The supernatant was visually inspected against white background for any discoloration (USP/NF. Official Monograph: Epinephrine Injection. 31/26 ed. Rockville, Md.: United States Pharmacopeial Convention, Inc.; 2008) and then filtered and diluted to make 4 mg/mL. The absorbance of diluted supernatant was measured at wavelength 310 nm using Genesys 10-s UV spectrophotometer (Thermo Fisher Scientific, Madison, USA) according to the USP method and criteria for the limit of adrenalone in epinephrine bitartrate solution (USP/NF. Official Monograph: Epinephrine Bitartrate. 31/26 ed. Rockville, Md.: United States Pharmacopeial Convention, Inc.; 2008). The absorbance of epinephrine bitartrate standard in the same solution and at the same concentration was used as a first control (control 1). The second control (control 2) was prepared to take in consideration the absorbance of any water-soluble excipients from the tablet that may interfere with the UV absorbance of epinephrine bitartrate oxidative products. Placebo tablets were dissolved and diluting using the same solvent and procedure above, then spiked with epinephrine bitartrate standard to make 4 mg/mL concentration. The absorptivity of all samples and controls was calculated by dividing the absorbance by the product of the concentration of the drug (g/L) and the path length (cm) of the cell used to measure the absorbance (USP/NF. Physical Tests: Spectrophotometery and Light-Scattering (851). 31/26 ed. Rockville, Md.: United States Pharmacopeial Convention, Inc.; 2008). An absorptivity of not more than 0.2 was considered acceptable according to the USP criteria for the limit of adrenalone in epinephrine bitartrate solution (USP/NF. Official Monograph: Epinephrine Bitartrate. 31/26 ed. Rockville, Md.: United States Pharmacopeial Convention, Inc.; 2008).

Data Analysis

The mean epinephrine content (dose) at $T_0$ for the manufactured tablets formulations before storage was obtained from the content uniformity test and was used as a control. The epinephrine contents (doses) in the sampled tablets for the three formulations and from each storage condition at various time-points and in control tablets were statistically compared by two-way ANOVA and Tukey-Kramer tests using statistical analysis software NCSS (NCSS, Kaysville, Utah). Differences were considered significant at $p<0.05$.

The epinephrine content (%) in the sampled tablets was calculated using the mean of epinephrine content in control tablets.

The absorptivity of oxidative products of epinephrine in the tablets from each formulation at each storage condition and in controls was statistically compared by two-way ANOVA and Tukey-Kramer tests.

The significance of existing trends for the stability of epinephrine or the increase of its oxidative products associated with the dose in the stored tablets was also tested.

Results

Hardness, disintegration time, and wetting time for the three tablet formulations, 10 mg, 20 mg, and 40 mg, are shown in Table 2.1.

TABLE 2.1

The hardness, disintegration time, and wetting time of the 10 mg, 20 mg, and 40 mg tablet formulations*†
In vitro Tablet Characteristics

| Formulations | H | CV | DT | CV | WT | CV |
|---|---|---|---|---|---|---|
| 10 mg tablets | 3.1 ± 0.1 | 6.4 | 7.7 ± 0.3 | 9.7 | 24.2 ± 0.9 | 8.8 |
| 20 mg tablets | 2.9 ± 0.1 | 11.6 | 12.0 ± 0.6 | 11.8 | 41.8 ± 3.6 | 21.1 |
| 40 mg tablets | 2.4 ± 0.1 | 12.4 | 13.5 ± 0.2 | 4.1 | 26.17 ± 1.8 | 17.0 |

*mean ± SD (n = 6)
†H indicates tablet hardness (kg); CV, coefficient of variation (%); DT, disintegration time (sec); WT, wetting time (sec).

All of the three tablet formulations were within USP specifications for weight variation, drug content uniformity, and friability (USP/NF. Physical Tests: Tablet Friability (1216). 26/21 ed. Rockville, Md.: United States Pharmacopeial Convention, Inc.; 2003; USP/NF. Physical Tests: Uniformity of Dosage Units (905). 31/26 ed. Rockville, Md.: United States Pharmacopeial Convention, Inc.; 2008). The mean±SD epinephrine doses in control tablets (at $T_0$) obtained from content uniformity test for 10 mg, 20 mg, and 40 mg epinephrine tablet formulations were 9.8±0.4 mg, 20.1±1.5 mg, and 38.0±1.8 mg, respectively.

There were no detectable visual changes in the 10 mg and 20 mg epinephrine tablet formulations stored for 6 and 12 months under the three storage conditions. Also, there were no detectable visual changes in the 40 mg epinephrine tablet formulation stored for 18 months at 5° C. with and without nitrogen flushing prior to storage. Pale yellow tablet discoloration was observed only in the 40 mg epinephrine tablet formulation stored for 18 months at 25° C. However, no yellow discoloration was visually detected against white background for the supernatant solution from the dissolved epinephrine tablets for UV absorbance measurements and for HPLC analysis.

Mean (±SD) epinephrine contents (dose and %) in the 10 mg and 20 mg epinephrine tablet formulations stored for 6 months, 12 months, and 7 years (only 10 mg tablet), and in the 40 mg epinephrine tablet formulation stored for 18 months and 7 years at 25° C., 5° C., and 5° C. with nitrogen flushing are shown in Tables 2.2A-B and 2.3, respectively.

Tables 2.2A-B below show mean±SD epinephrine content remaining in 10 mg (Table 2.2A) and 20 mg (Table 2.2B) epinephrine tablets stored at 25° C., 5° C., and 5° C. with nitrogen flushing (5° C.-$N_2$) for 6 months, 12 months, and 7 years (only 10 mg tablets).

Tables 2.2A-B: Epinephrine Content

TABLE 2.2A 10 mg epinephrine tablets; Mean ± SD content, mg (%)†

| Time | 25° C. | 5° C. | 5° C.-$N_2$ |
|---|---|---|---|
| 0 | 9.8 ± 0.4 (100) | | |
| 6 Months* | 9.2 ± 0.3 (95 ± 3) | 9.3 ± 0.4 (95 ± 4) | 9.4 ± 0.7 (96 ± 7) |
| 12 months* | 9.6 ± 0.3 (98 ± 3) | 9.7 ± 0.6 (99 ± 6) | 9.6 ± 0.3 (98 ± 3) |
| 7 years** | 8.9 ± 0.1 (91 ± 1) | 9.6 ± 0.1 (98 ± 1) | 8.9 ± 0.4 (91 ± 4) |

TABLE 2.2B 20 mg epinephrine tablets; Mean ± SD content, mg (%)†

| Time | 25° C. | 5° C. | 5° C.-$N_2$ |
|---|---|---|---|
| 0 | 20.1 ± 1.5 (100) | | |
| 6 Months* | 19.8 ± 1.1 (98 ± 6) | 19.8 ± 1.2 (98 ± 6) | 20.3 ± 0.8 (101 ± 4) |
| 12 months* | 19.4 ± 0.9 (96 ± 5) | 20.3 ± 0.7 (101 ± 3) | 20.9 ± 1.9 (104 ± 9) |
| 7 years** | NA | NA | NA |

*n=6
**n=3
†Epinephrine content (%) was calculated from mean epinephrine content in control tablets at $T_0$. Epinephrine content in all tablets was not significantly different from controls at the different storage conditions, p>0.05, and was within USP compedial limits for tablet content (85-115%).

Table 2.3 below shows mean±SD epinephrine content remaining in 40 mg epinephrine tablets stored at 25° C., 5° C., and 5° C. with nitrogen flushing (5° C.-$N_2$) for 18 months and 7 years.

Table 2.3: Epinephrine Content

TABLE 2.3

40 mg epinephrine tablets; Mean ± SD content, mg (%)†

| Time | 25° C. | 5° C. | 5° C.-$N_2$ |
|---|---|---|---|
| 0 | 38.0 ± 1.8 (100) | | |
| 18 months* | 37.5 ± 0.5 (99 ± 1) | 38.9 ± 1.5 (103 ± 4) | 38.5 ± 2.9 (101 ± 8) |
| 7 years** | 37.7 ± 1.0 (99 ± 3) | 38.1 ± 0.8 (100 ± 2) | 36.9 ± 0.3 (97 ± 1) |

*n = 6
**n = 3
†Epinephrine content (%) was calculated from mean epinephrine content in control tablets at $T_0$. Epinephrine content in all tablets was not significantly different from controls at the different storage conditions, p > 0.05, and was within USP compedial limits for tablet content (85-115%).

Epinephrine dose in the three tablet formulations at the three storage conditions did not differ significantly from control tablets over 7 years for 10 mg and 40 mg tablet formulations and 12 months for 20 mg tablet formulation. Also, the epinephrine content (%) for all the tested tablets was within the harmonized USP compendial limits, acceptance value (AV)<L1 (15%).

Figure 2:
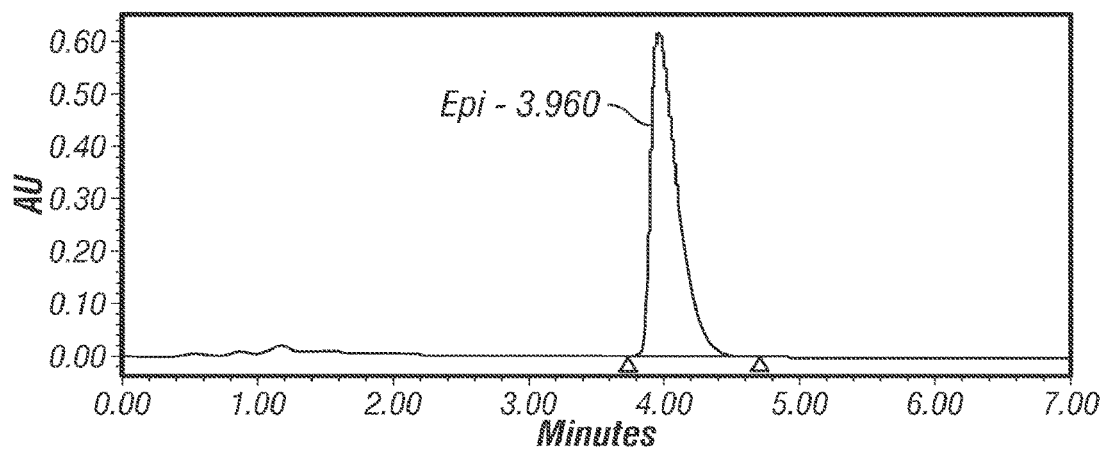
FIG. 2 is a HPLC Chromatogram of epinephrine bitartrate from the stored epinephrine tablets for 7 years.

There was no change in the shape of epinephrine peaks or a presence of a second peak in the HPLC chromatogram that indicates for the degradation of epinephrine or the existence of oxidative products in the analyzed tablets after storage (FIG. 2).

Figure 3:
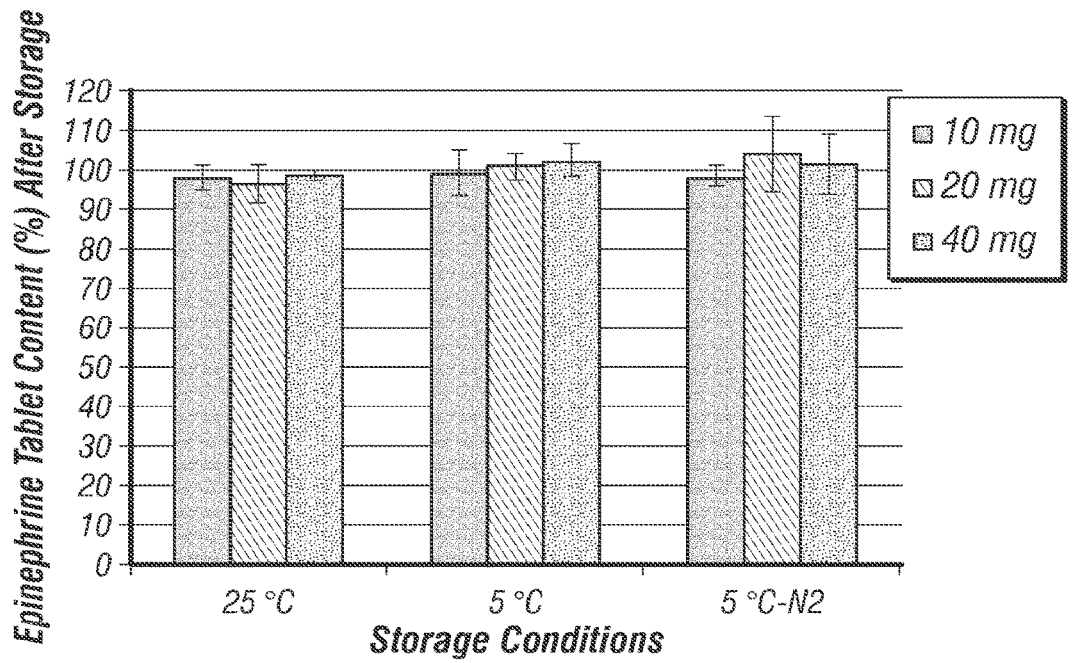
FIG. 3 is a graph showing mean±SD epinephrine tablet content (%) after storage at three storage conditions for three tablet formulations.

There was no significant trend in the stability of epinephrine associated with increasing epinephrine dose in the stored tablets at the various storage conditions (FIG. 3). FIG. 3 is a graph showing mean±SD (n=6) epinephrine tablet content (%) after storage at three storage conditions for three tablet formulations. Only tablets stored for 12 months and 18 months were plotted). p>0.05.

Figure 4:
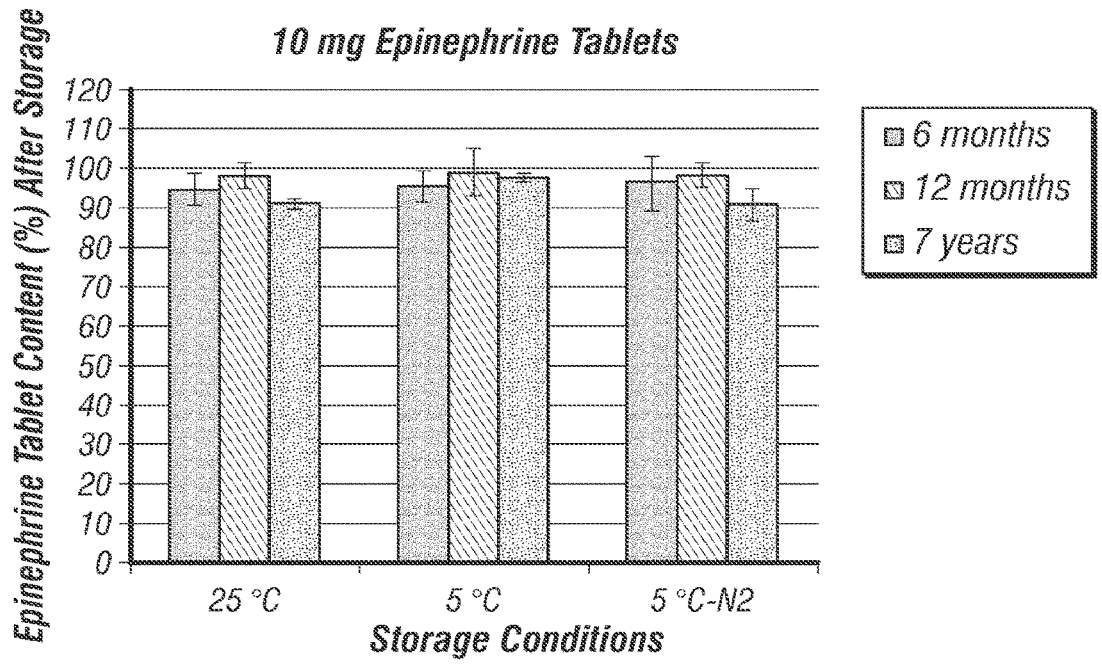
FIG. 4 is a graph showing mean±SD epinephrine content (%) in 10 mg epinephrine tablets after storage at three storage conditions (25°, 5° C., and 5° C.-$N_2$) for 6 months, 12 months, and 7 years.

Tablet content (%) of 10 mg epinephrine tablets after storage at three storage conditions (25°, 5° C., and 5° C.-$N_2$) for 6 months, 12 months, and 7 years is shown in FIG. 4.

Figure 5:
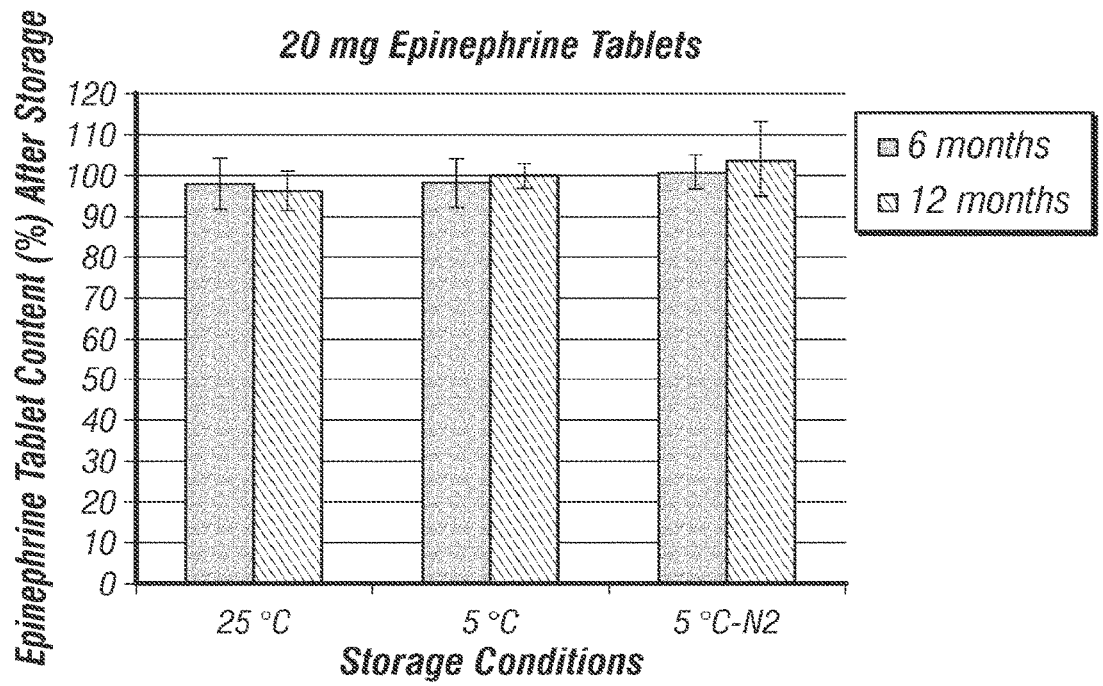
FIG. 5 is a graph showing mean±SD epinephrine content (%) in 20 mg epinephrine tablets after storage at three storage conditions (25°, 5° C., and 5° C.-$N_2$) for 6 months and 12 months.

Tablet content (%) of 20 mg epinephrine tablets after storage at three storage conditions (25°, 5° C., and 5° C.-$N_2$) for 6 months and 12 months is shown in FIG. 5.

Figure 6:
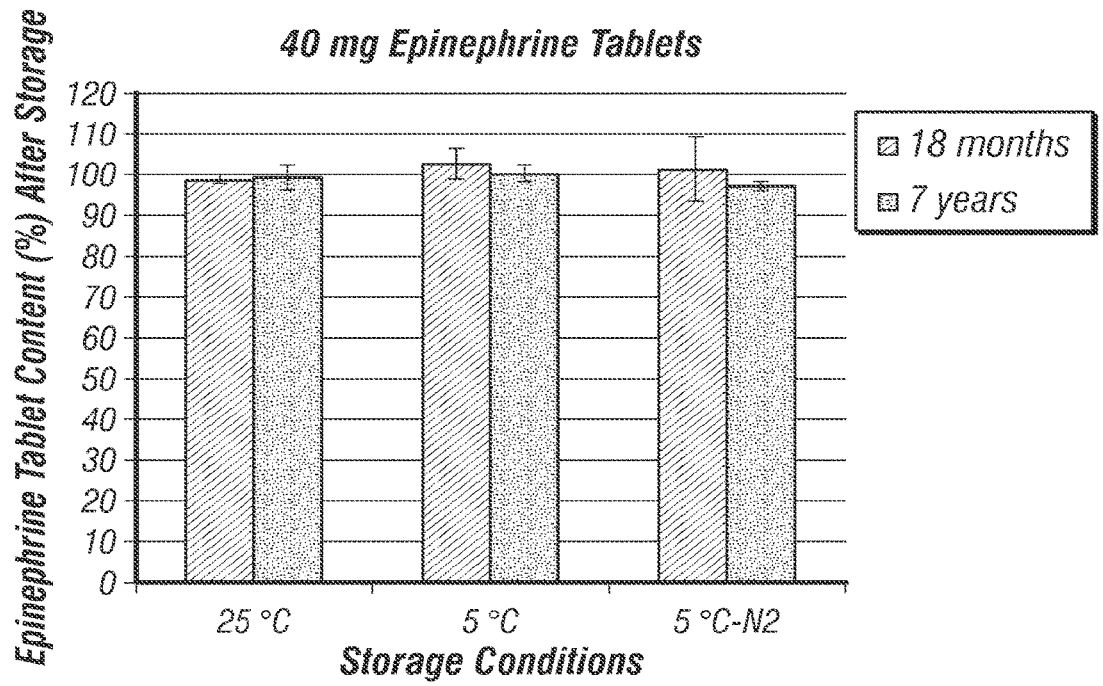
FIG. 6 is a graph showing mean±SD epinephrine content (%) in 40 mg epinephrine tablets after storage at three storage conditions (25°, 5° C., and 5° C.-$N_2$) for 18 months and 7 years.

Tablet content (%) of 40 mg epinephrine tablets after storage at three storage conditions (25°, 5° C., and 5° C.-$N_2$) for 18 months and 7 years is shown in FIG. 6.

In FIGS. 4-6, data was plotted using mean±SD and epinephrine content was not significantly different from control tablets, p>0.05, and was within USP compedial limits for tablet content (85-115%).

The absorptivity (mean±SD) of epinephrine tablets from each formulation stored at each storage condition for 7 years are shown in Table 2.4.

TABLE 2.4

Absorptivity of Oxidative Products of Epinephrine (Mean ± SD)*

| Formulations | 25° C. | 5° C. | 5° C.-$N_2$ |
|---|---|---|---|
| Epinephrine Bitartrate Solution (control 1) | 0.001 ± 0.000 | | |

TABLE 2.4-continued

Absorptivity of Oxidative Products of Epinephrine (Mean ± SD)*

| Formulations | 25° C. | 5° C. | 5° C.-$N_2$ |
|---|---|---|---|
| Epinephrine Tablets at $T_0$ (control 2) | 0.001 ± 0.000 | | |
| 10 mg tablets | 0.063 ± 0.001[a] | 0.003 ± 0.000[b] | 0.002 ± 0.000 |
| 20 mg tablets | 0.069 ± 0.001[a] | 0.003 ± 0.000[b] | 0.002 ± 0.000 |
| 40 mg tablets | 0.032 ± 0.001[a,c] | 0.001 ± 0.001 | 0.002 ± 0.0001 |

*n = 3
[a] p < 0.05, from controls (1 and 2) and epinephrine tablets stored at 5° C. and 5° C.-$N_2$.
[b] p < 0.05, from controls (1 and 2).
[c] p < 0.05, from 10 mg and 20 mg tablets stored at 25° C.

The absorptivity of oxidative products of epinephrine in the tablets from each formulation stored at each storage condition was below 0.2. However, the absorptivity of epinephrine tablets stored at 25° C. were significantly higher than controls and tablets stored at 5° C. and 5° C.-N2.

Figure 7:
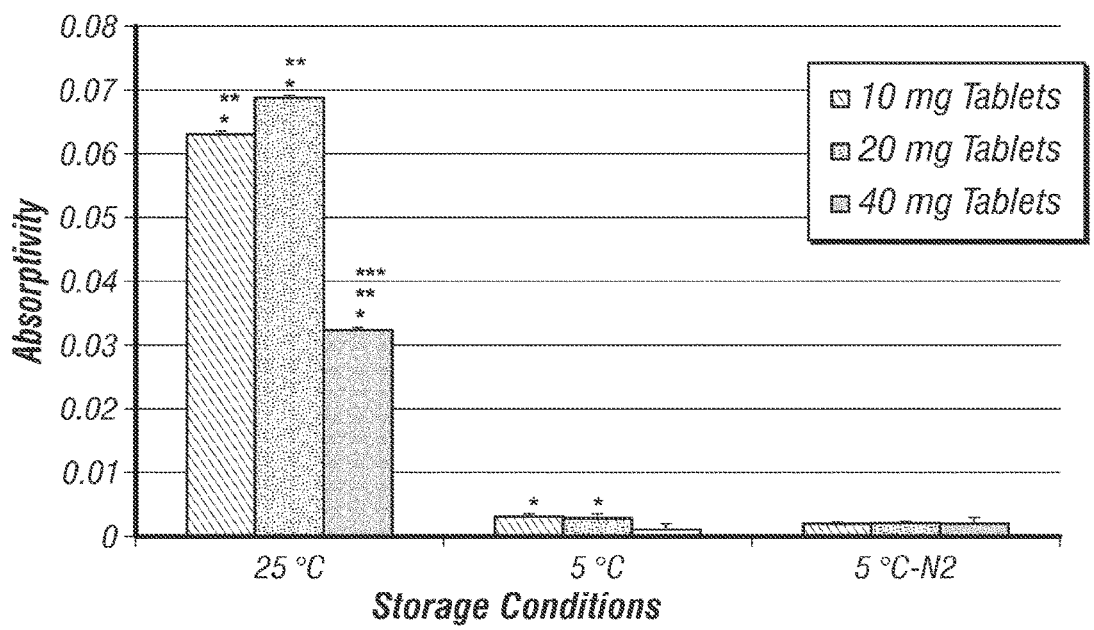
FIG. 7 is a graph showing mean±SD (n=3) absorpitvity of oxidative products of epinephrine from 10 mg, 20 mg, and 40 mg epinephrine tablets stored at three storage conditions (25°, 5° C., and 5° C.-$N_2$) for 7 years.

However, the absorptivity of 10 mg and 20 mg epinephrine tablets, but not the 40 mg tablets, stored at 5° C. were significantly higher than controls. Also, the absorptivity of 10 mg and 20 mg epinephrine tablets stored at 25° C. were significantly higher than 40 mg epinephrine tablets (FIG. 7). FIG. 7 is a graph showing absorptivity of three epinephrine tablet formulations after storage at three storage conditions for 7 years. Data was plotted using mean±SD (n=3). *p<0.05, from controls 1 and 2, p<0.05, from epinephrine tablets stored at 5° C. and 5° C.-N$_2$, *p<0.05, from 10 mg and 20 mg epinephrine tablets stored at 25° C. However, all tablets were below 0.2 (USP limit for impurities).

Discussion of Experiment and Results

Epinephrine in a dosage form exists only as ampoules for intravenous, intramuscular, or subcutaneous administration and prefilled autoinjectors for intramuscular self-administration by the patient for the emergency treatment of anaphylaxis. There is no tablet dosage form for epinephrine that exists in the market. Thus, there are no specific pharmacopeial guidelines or testing criteria for epinephrine tablet dosage form. The general harmonized USP compedial limits for tablet content is 85-115% of the label claim (the acceptance value (AV)≤the maximum allowed acceptance value (L1), which is 15%) (USP/NF. Physical Tests: Uniformity of Dosage Units (905). 31/26 ed. Rockville, Md.: United States Pharmacopcial Convention, Inc.; 2008).

The stability of epinephrine in solutions has been thoroughly investigated, and the optimal pH, storage conditions, and the required quantities of antioxidants to stabilize epinephrine have been determined (Connors et al., 1986, in *Chemical Stability of Pharmaceuticals: A Handbook for Pharmacists*, Wiley-Interscience Publication: New York; Rawas-Qalaji et al. *Ann Allergy Asthma Immunol* 102(6): 500-503 2009). The recommendations for the storage of epinephrine as a powder are documented in the USP (USP/NF. Official Monograph: Epinephrine Injection. 31/26 ed. Rockville, Md.: United States Pharmacopeial Convention, Inc.; 2008) and stated in the Material Safety Data Sheet (MSDS) (Material Safety Data Sheet: (−)-Epinephrine (+)-bitartrate salt. Saint Louis, Mo.: Sigma-Aldrich; [Jun. 19, 2009]). Although it would be expected that epinephrine should be stable for a longer period of time as a solid state more than a solution, there is no data about the time-frame for the stability of epinephrine powder at these recommended storage conditions. Also, there is no data about the stability of epinephrine in a tablet dosage form and whether the manufacturing processes and excipients selected for the formulation of these epinephrine tablets affect the stability of epinephrine on the long term.

The storage conditions that were selected for these experiments were based on the most common places for tablets to be stored at. However, dark and moisture-controlled packaging stored at room temperature is the most convenient packing material and place to store epinephrine tablets since these tablets are expected to be carried by allergic patients at all times. Epinephrine is sensitive to light, moisture, temperature, and oxygen (Gelone et al. Pharmaceutical and Medicinal Agents. In: Gerbino, P. editor. Remington: *The Science and Practice of Pharmacy* 21$^{st}$ edition, Baltimore, Md.: Lippincott Williams & Watkins; page 1386, 2005). Opaque containers containing desiccants were selected for storing the tablets during the experiments to control for the effect of light and moisture on epinephrine stability. The long-term effect of temperature and oxygen on the stability of epinephrine tablets were evaluated in these experiments.

It was reported that the hydroperoxide content in some of the commonly used excipients in pharmaceutical formulations may contribute to oxidative reactions in labile medications. Temperature increase was also found to increase the hydroperoxide content in these excipients. Microcrystalline cellulose, which is the main excipient used for the formulation of epinephrine tablets, however, was reported to contain minute levels of hydroperoxide (<10 nmole/g) and these levels did not increase after being exposed to elevated temperatures for four weeks (Wasylaschuk et al. *J Pharm Sci* 96(1):106-116 2007). Thus, the low content of hydroperoxide in the epinephrine tablet formulation might play an additional role to reduce epinephrine oxidation.

The results from the content uniformity test suggest that the manufacturing procedures and processes used in these experiments did not affect the stability of epinephrine in this tablet formulation. Direct compression method is commonly used for manufacturing tablets containing light, heat, or moisture-sensitive active pharmaceutical ingredient (Carlin, B A C. Direct Compression and the Role of Filler-Binders. In: Augsburger L L, Hoag S W, editors. *Pharmaceutical Dosage Forms: Tablets*. New York, N.Y.: Informa Healthcare USA, Inc. pages 173-216 2008). Also considering other measures like selecting excipients with low moisture content, maintaining the excipients under low humidity before mixing, using opaque containers flushed with nitrogen before mixing and storage, and compressing the powder mixture right after mixing might play a role as well in minimizing any oxidative reactions before and during the manufacturing of the tablets and during their storage.

The initial results from the HPLC analysis for the epinephrine content in 10 mg and 20 mg tablets showed that epinephrine was stable in this tablet formulation for up to 12 months (FIGS. 4 and 5) at the three storage conditions, 25° C. (room temperature), 5° C. (refrigerator temperature), and 5° C.-N$_2$ (refrigerator temperature and under nitrogen). Also, there was no tablet discoloration observed after 12 months of storage. As a result, the storage time for the 40 mg epinephrine tablets was extend for additional 6 months because it was anticipated that they could be more susceptible for degradation over a longer storage time more than the previous ones, i.e. 10 mg and 20 mg tablets, due to higher epinephrine content in these tablets.

The 40 mg epinephrine tablets were also stable after 18 months of storage at the three storage conditions (FIG. 6). Thus, the storage time was extended again for a total of 7 years for the lowest and highest doses, 10 mg and 40 mg epinephrine tablets. The HPLC analysis of these tablets at the three storage conditions showed that epinephrine was stable in this tablet formulation (FIGS. 4 and 6).

However, the 40 mg epinephrine tablets stored at 25° C. resulted in a pale or slightly yellow discoloration of the tablets that can be an indication for initial degradation of epinephrine and the formation of adrenolutin, a bright yellow oxidative product of epinephrine. (Bacq, Z M *Pharmacol Rev* 1:1-26 1949; Dhalla et al. *Mol Cell Biochem* 87(1):85-92 1989). From the statistical perspective, the epinephrine dose remaining in these tablets did not differ significantly from control tablets and was with the USP compendial limits for content uniformity.

A discoloration of epinephrine solution into pinkish color, due to oxidation to adrenochrome, or darker than slightly yellow color, due to oxidation to adrenolutin, or the presence of precipitate, due to conversion of oxidative products to melanin (*Br Med J* 5760(2):486 1971; Connors et al. *Chemi-* cal *Stability of Pharmaceuticals: A Handbook for Pharmacists* 2$^{nd}$ edition New York: Wiley-Interscience Publication 1986; Bacq, Z M *Pharmacol Rev* 1:1-26 1949), is not acceptable according to the USP standards for epinephrine injections (USP/NF. Official Monograph: Epinephrine Injection. 31/26 ed. Rockville, Md.: United States Pharmacopeial Convention, Inc.; 2008). However, the detection of only yellow discoloration upon visual inspection of epinephrine solution from epinephrine injection dosage form requires the measurement of its UV absorbance to make sure that it does not exceed the absorbance of its standard solution. Since epinephrine tablets do not exist in the market, there is no specific pharmacopeial procedure in place for testing the color and clarity of epinephrine bitartrate from epinephrine tablets or for testing the limits of adrenolutin in epinephrine tablet dosage form. Therefore, the measurement of UV absorbance of epinephrine bitartrate and its oxidative products from a tablet dosage form was performed according to the USP procedure and limit for adrenalone in epinephrine bitartrate as described earlier under Evaluation of Tablet Stability After Storage section. Adrenalone is an intermediate product for the epinephrine synthesis (Stolz, A F *Chem Ber* 37:4152 1904).

Despite of the lack of yellow discoloration of the supernatant solution for the 40 mg epinephrine tablets stored at 25° C. and although the tablets' discoloration was not darker than slight yellow color, their absorptivity and the absorbitivity of all the stored tablets were measured to further investigate the stability of epinephrine in the tablet formulation and to identify the existence of any trend in the stability at the various storage conditions and doses.

The absorptivity results of all the stored epinephrine tablets were below the USP limits for adrenalone in epinephrine bitartrate solution, which is 0.2, even for the tablets stored at 25° C. Therefore, the lack of discoloration and the low absorptivity of epinephrine bitartrate solution from epinephrine tablets, and the absence of a second peak for adrenolutin in the HPLC spectrum (Dhalla et al. *Mol Cell Biochem* 87(1):85-92 1989) supported by the high epinephrine content in the tablets suggest that the oxidative products of epinephrine in these tablets were insignificant or absent.

Although the epinephrine content (%) data from the different epinephrine tablets (10 mg, 20 mg, and 40 mg) stored at the same condition were not significantly different from each other (FIG. 3) and may not reflect any effect for the epinephrine dose used in the tablets on its own stability, the abosrpitivity data were more discriminative despite that the absorptivity of all the stored tablets at the different storage conditions were far below 0.2 (FIG. 7).

For the tablets stored at 25° C., although the absorptivity of all epinephrine tablets were significantly higher than controls due to the effect of temperature and oxygen on epinephrine stability, the absorbitivity of 40 mg epinephrine tablets was significantly lower than 10 mg and 20 mg tablets (FIG. 7). For the tablets stored at 5° C., the absorptivity of only 10 mg and 20 mg epinephrine tablets were significantly higher than controls, which represents only the effect of exposing epinephrine tablets to oxygen (FIG. 7). For the tablets stored at 5° C.-N$_2$, there was no significant difference in the absorbtivity between 40 mg epinephrine tablets and 10 mg and 20 mg tablets. Also the absorptivity of all these tablets was not different from controls, which clearly was due to the protection of epinephrine tablets from temperature and oxygen (FIG. 7).

Also, it indicates that the use of opaque containers and desiccants in the containers were sufficient to reduce the exposure of epinephrine tablets to light and humidity, respectively, which helped in maintaining the stability of epinephrine as well.

Despite the lack of significant trend for the effect of epinephrine dose on the epinephrine absorpitivity and thus the stability of epinephrine, these observations may suggest that higher epinephrine content in the tablets stored at less optimal storage conditions reduces the susceptibility of its own degradation. Also, the results from this study shows that epinephrine in this fast-disintegrating tablet formulation are stable for at least 7 years at less optimal storage conditions. However, limiting the exposure of these tablets to oxygen and more importantly storing them at lower temperatures will reduce epinephrine oxidation. Further studies are useful to evaluate the stability of these epinephrine tablets at 25° C. under N$_2$.

Example 3: Fabrication and Characterization of Epinephrine Nanoparticles Using High Shear Fluid Processor (Microfluidizer)

The feasibility of the fabrication of epinephrine nanoparticles using a high shear fluid processor (microfluidizer) was described in prior patent applications; U.S. Provisional Patent Application No. 61/550,359, filed on Oct. 21, 2011 and International Application No. PCT/US2011/26604, filed on Mar. 1, 2011.

Epinephrine IM (intramuscular) injection in the thigh is the recommended route of administration for first aid treatment of anaphylaxis in the community. Due to drawbacks of this injection, alternative methods of administration are being explored.

The instant inventors developed a fast-disintegrating epinephrine tablet suitable for SL (sublingual) administration (Rawas-Qalaji et al. *AAPS Pharm Sci Tech* 7:E41 2006). Sublingual administration of 40 mg epinephrine as the bitartrate salt using these tablets resulted in a rate and an extent of epinephrine absorption similar to that achieved following intramuscular injections of 0.3 mg epinephrine in the thigh (Rawas-Qalaji et al. *J Allergy Clin Immunol* 117:398-403 2006). Sublingual doses ranging from 5 to 40 mg epinephrine as the bitartrate salt were studied to achieve equivalent plasma concentrations.

Without being bound by theory, it is thought that by fabricating epinephrine into nanoparticles and incorporating penetration enhancers and mucoadhesives (if needed) into the tablet formulation, absorption of sublingually-administered epinephrine will significantly increase and will result in reduction of the sublingual epinephrine dose required.

Fabrication of Nanoparticles

Nanoparticles were fabricated from epinephrine base and epinephrine bitartrate (Bit) using high energy fluidization (microfluidization) techniques. These techniques involve the use of various concentrations in various solvents, particularly water and isopropanol, at various temperatures and pressures ranging from about 8,000 psi to 30,000 psi and to about 8.3° to 43.3° C. under various passes. Particle size was measured before size reduction using a Mastersizer (Malvern) and/or a NiComp 370. Submicron Particle Sizer (NiComp) and nano-sized particles were confirmed using laser diffraction techniques (Zetasizer, Malvern). The particles were lyophilized (freeze-dried) using a bench top lyophilizer (ART Inc.) or dried by speed vacuum concentrator.

Methods

Selection of Vehicle for Shear Fluid Processing: The carrier vehicle for epinephrine base or epinephrine bitartrate was selected based on least solubilizing capacity at room temperature and toxicity of that vehicle. Two milligrams of epinephrine bitartrate was dissolved in 1 ml methanol, isopropyl alcohol, acetonitrile, acetone, hexane, chloroform, or tetrahydrofuran, ethyl acetate by vortexing for 15 minutes. Supernatant solution was withdrawn and filtered through 0.22 µm nylon syringe filters to be analyzed for the quantification of dissolved epinephrine.

High Performance Liquid Chromatography (HPLC) Analysis: Samples from the solubility study were analyzed using a PerkinElmer HPLC system with ultraviolet (UV) detector and Econspher $C_{18}$, 4.6×150 mm, 3 µm column (Alltech). Analysis and condition were performed according to USP $26^{th}$ edition, 2003 "Epinephrine Injection Monograph."

Nanoparticles Fabrication: Epinephrine bitartrate or base was suspended in isopropyl alcohol at various concentrations to make 6 mL samples (0.7, 1.4, 2.8, 3.5, and 4.5 mg/ml). Samples were prepared in triplicates for each concentration, n=3. All prepared samples were processed using LV-1 High Shear Fluid Processor "Microfluidizer" (Microfluidics, Newton, Mass.) equipped with G10Z reaction chamber under various pressures ranging from 15 to 30 KPsi for single or several passes. The microfluidizer-receiving coil was immersed in ice to reduce the heat produced during the process for heat-sensitive drugs. The particle size and potential of the produced nanosuspension were measured. The nanosuspension was centrifuged at 15,000 rpm and 15° C. for 30 minutes to collect the nanoparticles, and the solvent was then removed. The collected nanoparticles were completely dried by speed vacuum concentrator or lyophilization.

Nanoparticle Characterization: The particle size distribution and zeta potential of the nanosuspension was measured before and after size reduction by volume and by intensity using Mastersizer (Malvern) and Zetasizer Nano-ZS90 (Malvern), respectively. The average of 3 measurements for each sample was reported. Stability of epinephrine and epinephrine bitartrate was monitored by visually inspecting the color of the processed suspension and by using Fourier Transform InfraRed (FT-IR, PerkinElmer Inc) for the dried samples.

Results

Selection of Vehicle for Shear Fluid Processing: In order to determine suitable vehicles to suspend epinephrine base or epinephrine bitartrate (Bit) for nanoparticle fabrication, solubility studies were carried out to select the vehicles that minimally solubilize the drug.

TABLE 3.1

| | Solubility |
|---|---|
| Sample Name | Amount Dissolved (µg/ml) |
| Epinephrine Base solubility in water | 53.37 |
| Epinephrine Bit solubility in methanol | 209.01 |
| Epinephrine Bit solubility in isopropyl alcohol | 12.30 |
| Epinephrine Bit solubility in acetonitrile | 15.46 |
| Epinephrine Bit solubility in acetone | 31.28 |
| Epinephrine Bit solubility in hexane | 0.53 |
| Epinephrine Bit solubility in chloroform | 1.87 |
| Epinephrine Bit solubility in tetrahydrofuran (THF) | 155.18 |
| Epinephrine Bit solubility in ethyl acetate | 12.60 |

Figure 8:
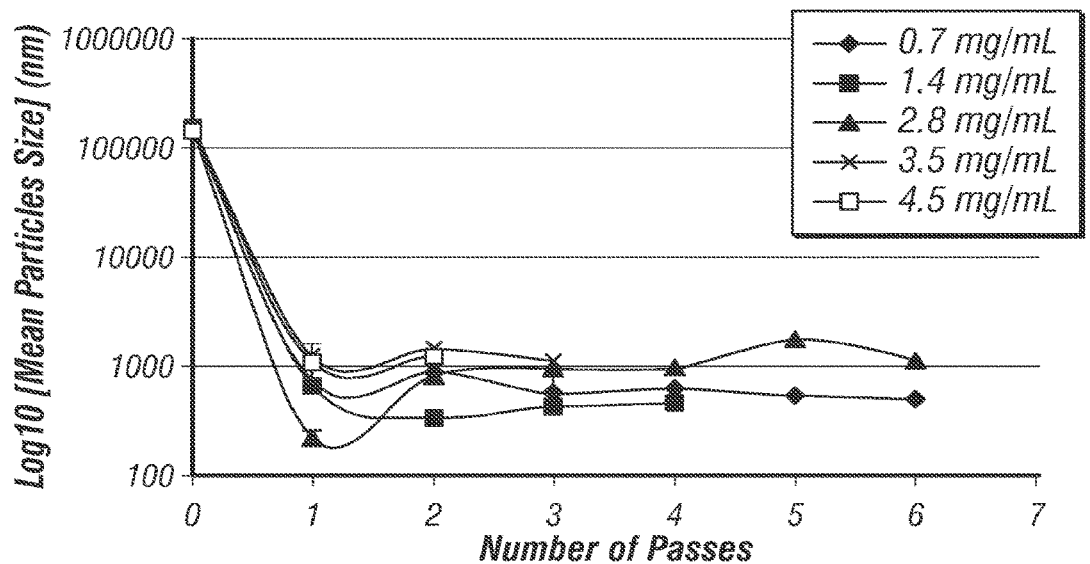
FIG. 8 is a graph showing mean±SD (n=3) size of epinephrine bitartrate (Z-Average, nm) for several concentrations (0.7 mg/ml, 1.4 mg/ml, 2.8 mg/ml, 3.5 mg/ml, and 4.5 mg/ml) following several passes at 30 KPsi.

Results of the Fabrication of Epinephrine Bitartrate Nanoparticles a): Mean size of epinephrine bitartrate (Z-Average) following several passes at 30 KPsi is shown below in Table 3.2 and in FIG. 8. FIG. 8 is a graph showing Mean±SD (n=3) size of epinephrine bitartrate (Z-Average, nm) for several concentrations (0.7 mg/ml, 1.4 mg/ml, 2.8 mg/ml, 3.5 mg/ml, and 4.5 mg/ml) following several passes at 30 KPsi.

TABLE 3.2

Mean ± SD* particles size distribution of epinephrine bitartrate (Z-Average, nm, and pdi) for several concentrations (0.7 mg/ml, 1.4 mg/ml, 2.8 mg/ml, 3.5 mg/ml, and 4.5 mg/ml) following several passes at 30 KPsi.
Mean ± SD* particles size (nm) and polydispersity (pdi)

| Number of Passes | 0.7 mg/ml | 1.4 mg/ml | 2.8 mg/ml |
|---|---|---|---|
| 0† | 131,800 ± 10500 | 131,800 ± 10500 | 131,800 ± 10500 |
| 1 | 706 + 289 (0.257 + 0.060) | 665 + 47 (0.239 + 0.044) | 249 + 38 (0.490 + 0.134) |
| 2 | 879 ± 376 (0.119 ± 0.052) | 339 ± 34 (0.158 ± 0.021) | 827 ± 114 (0.649 ± 0.236) |
| 3 | 573 ± 329 (0.167 ± 0.026) | 422 ± 40 (0.190 ± 0.022) | 971 ± 124 (0.243 ± 0.112) |
| 4 | 618 ± 267 (0.217 ± 0.035) | 456 ± 40 (0.178 ± 0.039) | 976 ± 163 (0.219 ± 0.035) |
| 5 | 539 ± 65 (0.170 ± 0.070) | | 1713 ± 36 (0.099 ± 0.043) |
| 6 | 501 ± 34 (0.195 ± 0.067) | | 1161 ± 127 (0.836 ± 0.268) |

| Number of Passes | 3.5 mg/ml | 4.5 mg/ml |
|---|---|---|
| 0† | 131,800 ± 10500 | 131,800 ± 10500 |
| 1 | 1211 + 389 (0.335 + 0.112) | 1091 + 43 (0.321 + 0.060) |
| 2 | 1418 ± 79 (0.576 ± 0.080) | 1242 ± 28 (0.315 ± 0.055) |
| 3 | 1116 ± 135 (0.506 ± 0.067) | |
| 4 | | |
| 5 | | |
| 6 | | |

*n = 3
†n = 6, before processing, the $10^{th}$ percentile (Dv0.1), median (Dv0.5), and $90^{th}$ percentile (Dv0.9) were 39.8 ± 3.0 µm, 113.6 ± 9.1 µm, and 254.8 ± 20.1, respectively.

Epinephrine bitartrate size reduction resulted in various sizes based on the concentration of the suspension processed. Samples at lower concentrations required several passes to reduce the particle size; however, samples at higher concentrations were very condensed to be processed and required several passes before particle size was reduced. Over processing the sample beyond the number of optimal passes required can result in aggregation of the reduced particles and an increase in their size. The optimal concentration for epinephrine bitartrate suspended in isopropyl alcohol (IPA) was 2.8 mg/ml that resulted in the lowest particle size and uniform narrow size range after only one pass.

Results of the Fabrication of Epinephrine Bitartrate Nanoparticles b): Particle size distribution and zeta potential of epinephrine bitartrate following several passes at 30 KPsi is shown in FIGS. 9-13.

Figure 9:
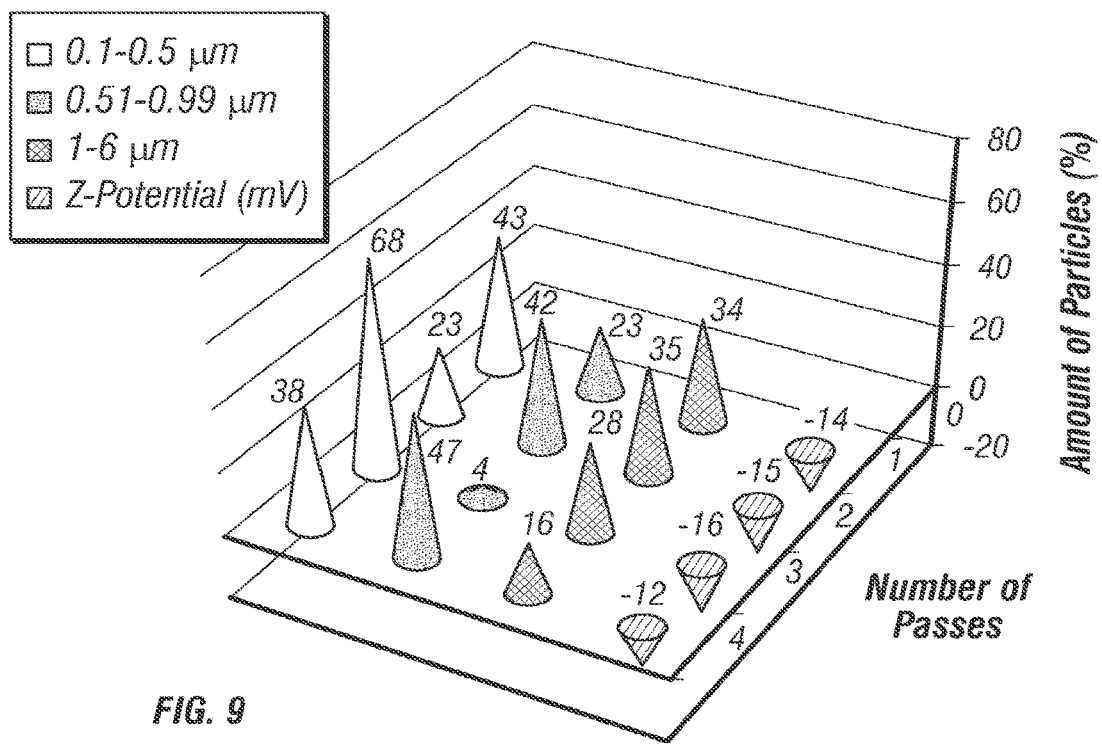
FIG. 9 is a graph showing mean (n=3) particle size distribution and zeta potential of 0.7 mg/ml epinephrine bitartrate following several passes at 30 KPsi.

At 0.7 mg/ml epinephrine bitartrate (n=3) in isopropyl alcohol (IPA), particles were distributed over a wide size-range and resulted in less negative zeta potential due to high polydispersity despite several passes (FIG. 9).

Figure 10:
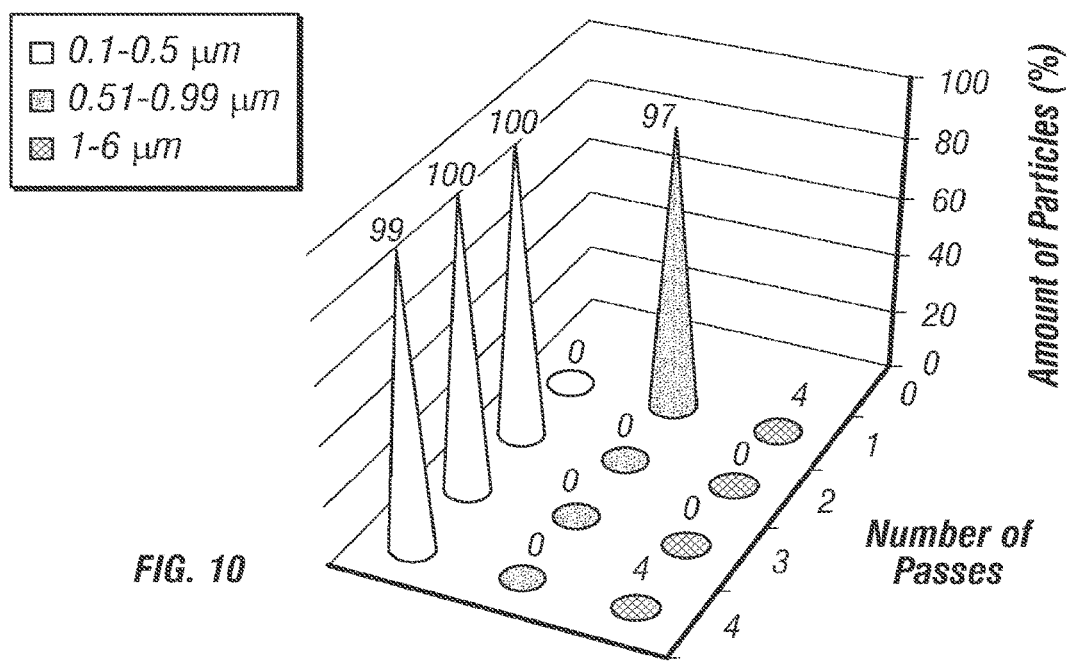
FIG. 10 is a graph showing mean (n=3) particle size distribution of 1.4 mg/ml epinephrine bitartrate following several passes at 30 KPsi.

At 1.4 mg/ml epinephrine bitartrate (n=3) in IPA, particle distribution was uniform and required two passes (at 30 KPsi) to achieve optimal size (FIG. 10).

Figure 11:
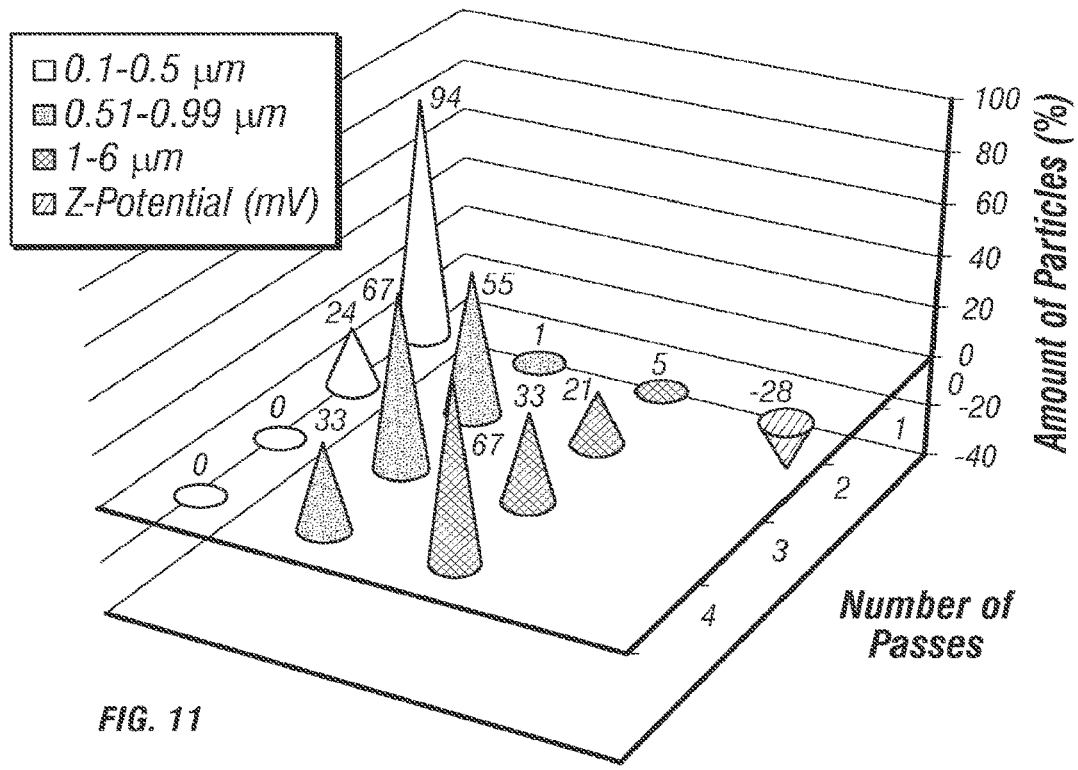
FIG. 11 is a graph showing mean (n=3) particle size distribution and zeta potential of 2.8 mg/ml epinephrine bitartrate following several passes at 30 KPsi.

At 2.8 mg/ml epinephrine bitartrate (n=3) in IPA, particle distribution was uniform and particle size was optimal following one pass only, which is reflected in more negative zeta potential (FIG. 11). Further processing caused the particles to aggregate and increase and the distribution became less uniform.

Figure 12:
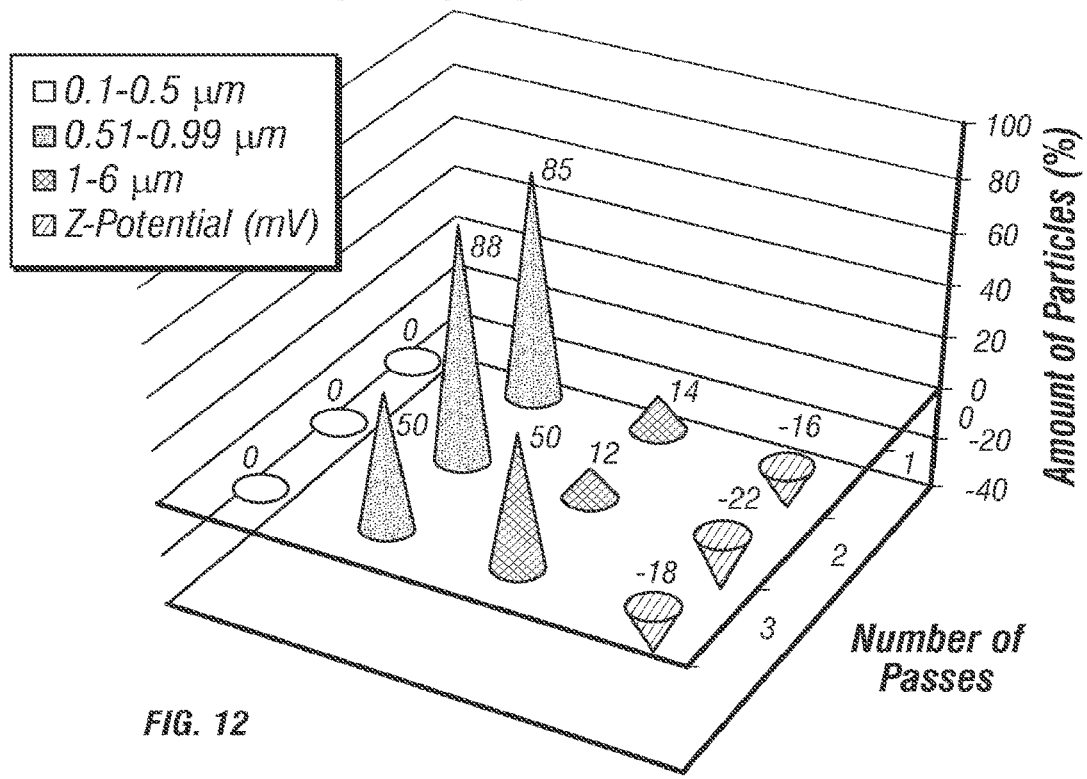
FIG. 12 is a graph showing mean (n=3) particle size distribution and zeta potential of 3.5 mg/ml epinephrine bitartrate following several passes at 30 KPsi.

At 3.5 mg/ml epinephrine bitartrate (n=3) in IPA, particle distribution was slightly not uniform the first two passes and particle size was at a higher range (FIG. 12). Further processing caused the particles to aggregate and increase and the distribution became even less uniform.

Figure 13:
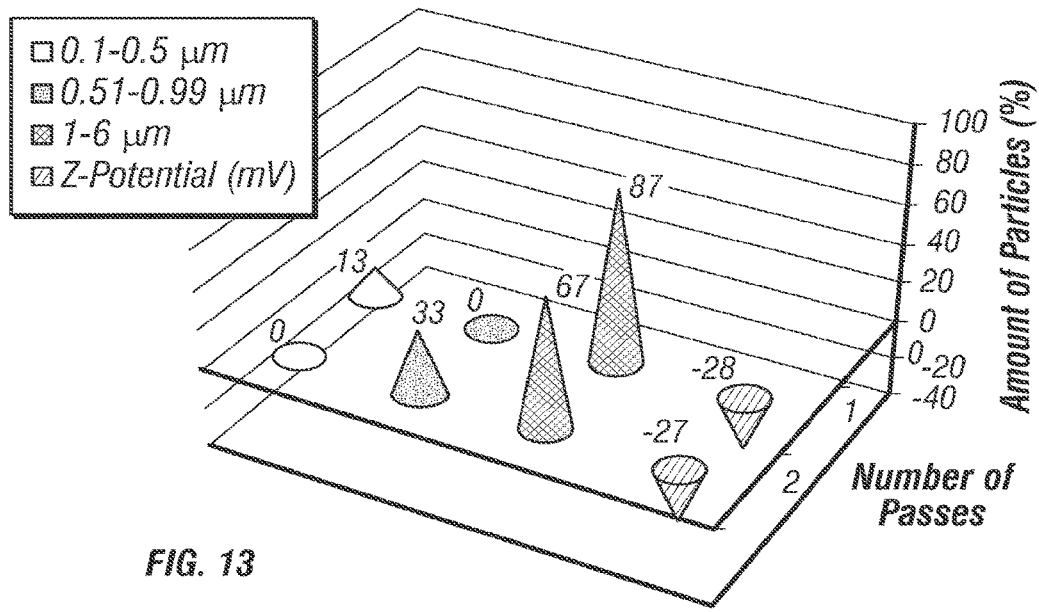
FIG. 13 is a graph showing mean (n=3) particle size distribution and zeta potential of 4.5 mg/ml epinephrine bitartrate following several passes at 30 KPsi.

At 4.5 mg/ml epinephrine bitartrate (n=3) in IPA, particle distribution was considerably not uniform and particle size was in the higher range (FIG. 13).

Figure 14:
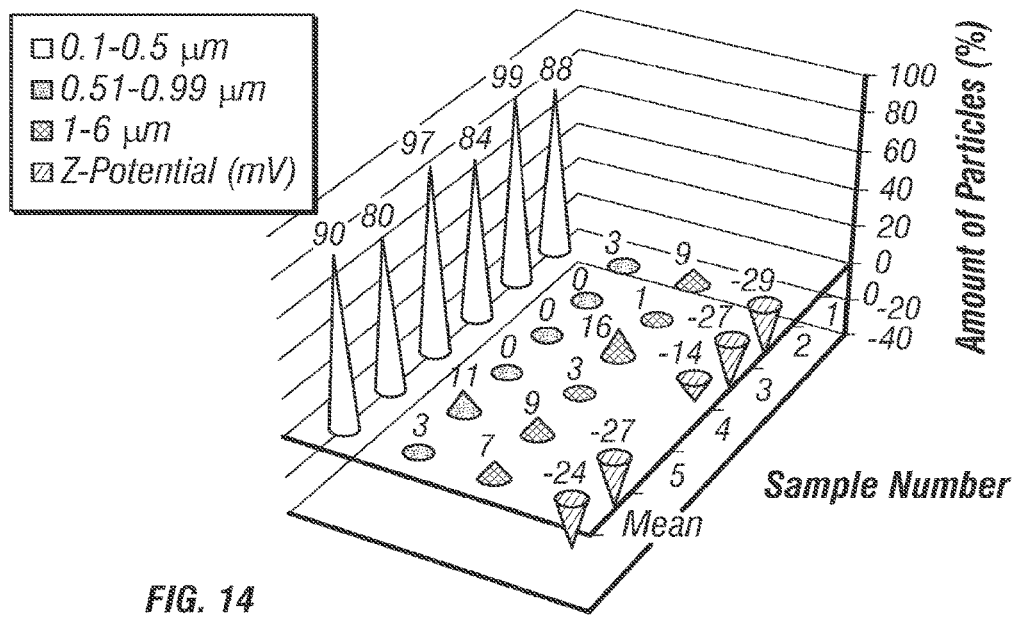
FIG. 14 is a graph showing reproducibility (n=5) of particle size distribution and zeta potential of 2.8 mg/ml epinephrine bitartrate following one pass at 30 KPsi.

Reproducibility of the Fabrication of Epinephrine Bitartrate Nanoparticles: Five samples of 2.8 mg/ml epinephrine bitartrate in IPS were processed at 30 KPsi for one pass. Mean±SD size of epinephrine bitartrate (Z-Average) was 230±39 nm with a coefficient of variation (RSD) of 17% (Table 3.3). Mean±SD particle size distribution was uniform and size was mainly (90±8% with RSD of 9%) at the lower range (187±34 nm with RSD of 18%) and mean±SD zeta potential of epinephrine bitartrate was −24±7 my (FIG. 14).

TABLE 3.3

Mean Size* of epinephrine bitartrate (Z-Average, nm) for 2.8 mg/ml concentration following one pass at 30 KPsi

| Sample Number | Mean Size (Z-Average, nm) |
|---|---|
| 1 | 263 |
| 2 | 279 |
| 3 | 196 |
| 4 | 199 |
| 5 | 211 |

*n = 3 measurements
Mean 230
SD 39
RSD (%) 17

Figure 15:
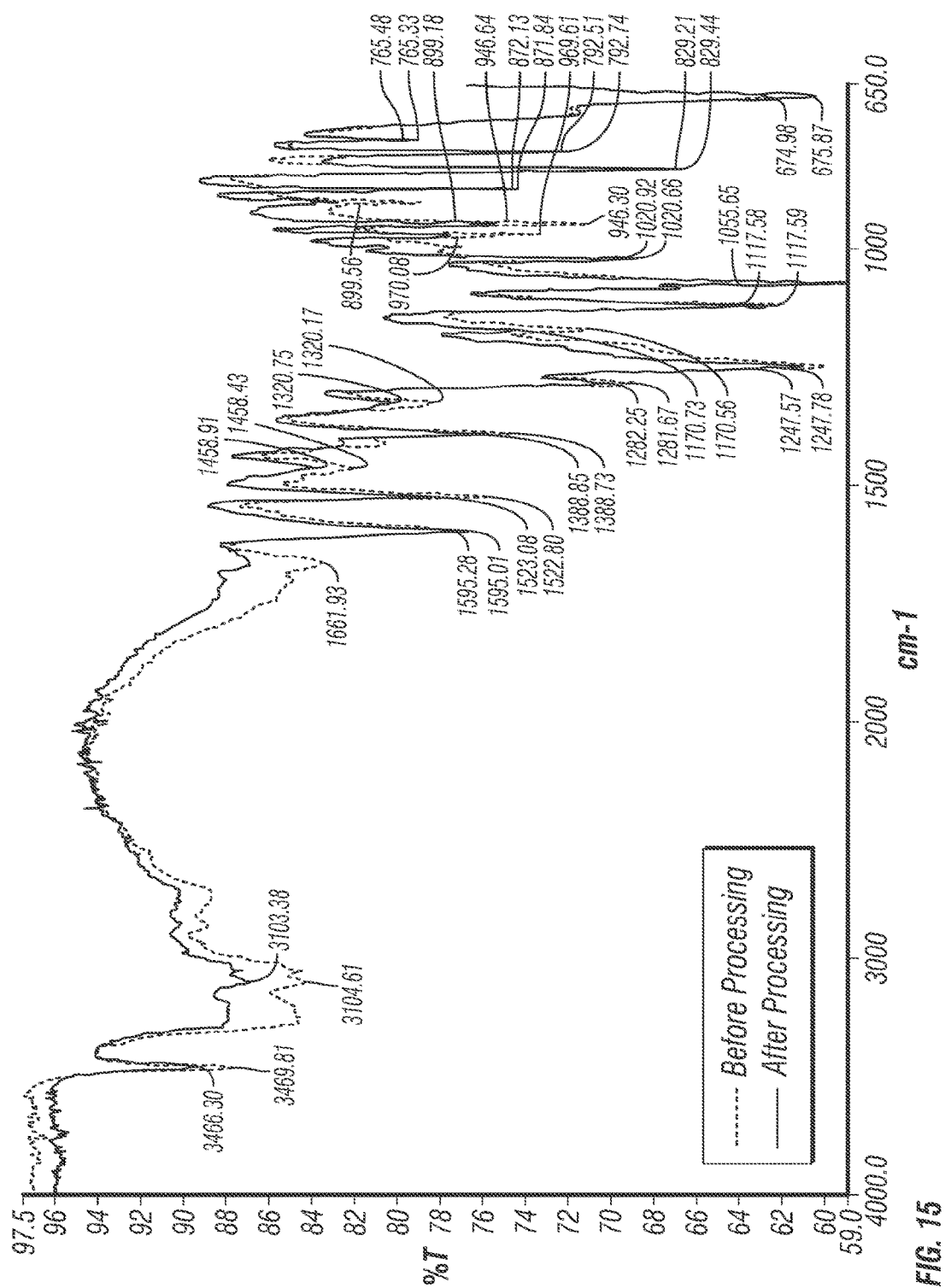
FIG. 15 is a FTIR spectra of epinephrine bitartrate before and after processing using 2.8 mg/ml sample concentration processed at 30 KPsi.

Stability of the Fabricates Epinephrine Bitartrate Nanoparticles: There was no change in color of the fabricated nanosuspension at the various concentrations. The FTIR (Fourier transform infrared) spectra of epinephrine bitartrate dried particles were similar before and after processing using 2.8 mg/ml sample concentration (FIG. 15).

Based upon the above results, it is evident that the fabrication of nanoparticles using a high shear fluid processor (Microfluidizer) was successful. The selection of optimal sample concentration to be processed at the optimal pressure resulted in reproducible, uniform, stable, and small particle size range. For epinephrine bitartrate, particles were reduced from 150.7±5 µm to 223±35 nm at sample concentration of 2.8 mg/ml and pressure of 30 KPsi that was produced for only one pass.

Conclusions Based on Results of Experiments of Examples 1-3

Fast-disintegrating sublingual epinephrine tablets (disclosed in related application: U.S. Utility patent application Ser. No. 11/530,360, filed on Sep. 8, 2006) which retain sufficient hardness to withstand shipping and handling and disintegrate to release epinephrine rapidly (<15 sec) (Rachid et al. *AAPS PharmSci Tech* 11(2):550-557 2010; Rawas-Qalaji et al. *Drug Dev Ind Pharm* 33(5):523-530 2007; Rawas-Qalaji et al. *AAPS PharamSci Tech* 7(2): Article 41 2006), have shown to be bioequivalent to epinephrine intramuscular injection in a validated rabbit model (Rawas-Qalaji et al. *J Allergy Clin Immunol* 117(2):398-403 2006; Rawas-Qalaji et al. *Biopharm Drug Dispos* 27(9):427-435 2006).

Incorporation of epinephrine nanoparticles fabricated using a high shear fluid processor (Microfluidizer) into the fast-disintegrating tablets, enhances the sublingual bioavailability of epinephrine.

Epinephrine was shown to be stable in these fast-disintegrating sublingual tablets for at least seven years. However, efforts should still be made to limit or minimize exposure of the tablets to oxygen and temperature.

The fast-disintegrating, taste-masked epinephrine sublingual tablets described herein are suitable for Phase I studies in humans and have the potential to transform the treatment of anaphylaxis and other conditions responsive to epinephrine.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The compositions, epinephrine nanoparticles, pharmaceutical tablets, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. A sublingual composition formulated as a fast-disintegrating tablet, the sublingual composition comprising:
   a pharmaceutically-effective dose of an active ingredient consisting of approximately 10 mg to approximately 40 mg of nanoparticles of epinephrine bitartrate, the nanoparticles of epinephrine bitartrate having a mean size (Z-average) ranging from about 279 nm to about 196 nm; and
   at least one pharmaceutically-acceptable carrier.

2. The sublingual composition in accordance with claim 1, wherein the at least one pharmaceutically-acceptable carrier is selected from the group consisting of diluents, binders, disintegrants, flavorings, fillers, and lubricants.

3. The sublingual composition in accordance with claim 1, wherein the sublingual composition comprises at least three pharmaceutically-acceptable carriers selected from the group consisting of diluents, binders, disintegrants, flavorings, fillers, and lubricants.

4. The sublingual composition in accordance with claim 3, wherein the at least three pharmaceutically-acceptable carriers include a filler, a lubricant, and a disintegrant.

5. The sublingual composition in accordance with claim 1, wherein the sublingual composition further comprises at least one of a penetration enhancer, a mucoadhesive, a taste enhancer, and a sweetening agent and mouthfeel enhancer.

6. The sublingual composition in accordance with claim 1, wherein the fast-disintegrating tablet is stable and remains pharmaceutically-effective after a period ranging from approximately six months to seven years.

7. A pharmaceutical composition formulated as an oral disintegrating tablet (ODT) for buccal or sublingual administration, the pharmaceutical composition comprising:
   a pharmaceutically-effective dose of an active ingredient consisting of approximately 40 mg of stabilized epinephrine bitartrate nanoparticles; and
   at least one non-medicinal ingredient (NMI); whereby, upon disintegration of the ODT post administration, the ODT increases absorption of buccally or sublingually-administrated epinephrine, the increases in absorption resulting from formulation of the pharmaceutical composition with the stabilized epinephrine bitartrate nanoparticles.

8. The pharmaceutical composition in accordance with claim 7, wherein the at least one non-medicinal ingredient (NMI) is selected from the group consisting of a filler, a lubricant, a disintegrant, a penetration enhancer, a mucoadhesive, a taste enhancer, and a sweetening agent and mouthfeel enhancer.

9. The pharmaceutical composition in accordance with claim 7, wherein the pharmaceutical composition comprises at least five non-medicinal ingredients.

10. The pharmaceutical composition in accordance with claim 7, wherein the stabilized epinephrine bitartrate nanoparticles have a mean size (Z-average) ranging from about 279 nm to about 196 nm.

11. Stabilized epinephrine bitartrate nanoparticles for formulation in an oral disintegrating tablet (ODT), the stabilized epinephrine bitartrate nanoparticles produced by a method comprising:
   a) forming a mixture consisting of non-nanosized epinephrine bitartrate salt particles and a solvent by combining a pre-determined amount of the non-nanosized epinephrine bitartrate salt particles and the solvent in a reaction chamber;
   b) exposing the mixture to one pass at a pressure of 30 KPsi and a pre-determined temperature; thereby reducing size of the non-nanosized epinephrine bitartrate salt particles to obtain epinephrine bitartrate nanoparticles, the epinephrine bitartrate nanoparticles having a mean size (Z-average) ranging from about 279 nm to about 196 nm; and
   c) lyophilizing the epinephrine bitartrate nanoparticles obtained from carrying out steps a) and b) to produce stabilized epinephrine bitartrate nanoparticles for formulation in an ODT.

12. The sublingual composition in accordance with claim 4, wherein the filler is microcrystalline cellulose, the lubricant is magnesium stearate, and the disintegrant is a low hydroxylpropyl ether of cellulose (L-HPC).

13. The sublingual composition in accordance with claim 5, wherein the sublingual composition comprises a taste enhancer and a sweetening agent and mouthfeel enhancer.

14. The pharmaceutical composition in accordance with claim 9, wherein the at least five non-medicinal ingredients include a filler, a lubricant, a disintegrant, a taste enhancer, and a sweetening agent and mouthfeel enhancer.

15. The pharmaceutical composition in accordance with claim 14, wherein the filler is microcrystalline cellulose, the lubricant is magnesium stearate, the disintegrant is a low hydroxypropyl ether of cellulose (L-HPC), the taste enhancer is citric acid, and the sweetening agent and mouthfeel enhancer is mannitol.

16. The pharmaceutical composition in accordance with claim 14, comprising by weight percent about 36% stabilized epinephrine bitartrate nanoparticles, about 6% microcrystalline cellulose filler (MMC PH-M-06), about 33% microcrystalline cellulose filler (MMC PH-301), about 2% lubricant, about 4% disintegrant, about 1% taste enhancer, and about 17% sweetening agent and mouthfeel enhancer.

17. The sublingual composition in accordance with claim 13, wherein the taste enhancer is citric acid and the sweetening agent and mouthfeel enhancer is mannitol.

* * * * *